(12) United States Patent
Beswick

(10) Patent No.: US 10,512,651 B2
(45) Date of Patent: Dec. 24, 2019

(54) INHIBITION OF MK2 IN THE TREATMENT OF CANCER

(71) Applicant: STC.UNM, Albuquerque, NM (US)

(72) Inventor: Ellen Janine Beswick, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 15/506,421

(22) PCT Filed: Aug. 21, 2015

(86) PCT No.: PCT/US2015/046238
§ 371 (c)(1),
(2) Date: Feb. 24, 2017

(87) PCT Pub. No.: WO2016/032882
PCT Pub. Date: Mar. 3, 2016

(65) Prior Publication Data
US 2018/0221382 A1   Aug. 9, 2018

Related U.S. Application Data

(60) Provisional application No. 62/041,491, filed on Aug. 25, 2014.

(51) Int. Cl.
| | | |
|---|---|---|
| *A61K 31/554* | (2006.01) | |
| *A61K 38/00* | (2006.01) | |
| *A61K 31/553* | (2006.01) | |
| *A61K 31/167* | (2006.01) | |
| *A61K 45/06* | (2006.01) | |
| *A61K 31/4709* | (2006.01) | |
| *A61K 31/496* | (2006.01) | |
| *A61K 31/551* | (2006.01) | |
| *A61P 35/00* | (2006.01) | |
| *A61K 31/165* | (2006.01) | |

(52) U.S. Cl.
CPC .......... *A61K 31/553* (2013.01); *A61K 31/165* (2013.01); *A61K 31/167* (2013.01); *A61K 31/4709* (2013.01); *A61K 31/496* (2013.01); *A61K 31/551* (2013.01); *A61K 38/005* (2013.01); *A61K 45/06* (2013.01); *A61P 35/00* (2018.01); *A61K 2300/00* (2013.01)

(58) Field of Classification Search
CPC .. A61K 2300/00; A61K 38/005; A61K 38/00; A61K 31/554
See application file for complete search history.

(56) References Cited

U.S. PATENT DOCUMENTS

| | | | |
|---|---|---|---|
| 6,214,821 B1 | 4/2001 | Daoud | |
| 8,741,849 B2 * | 6/2014 | Panitch | A61K 38/005 514/18.9 |
| 2004/0209897 A1 | 10/2004 | Vernier et al. | |
| 2008/0293640 A1 | 11/2008 | Brophy et al. | |
| 2010/0158968 A1 * | 6/2010 | Panitch | A61K 38/16 424/422 |
| 2010/0179143 A1 * | 7/2010 | Adams | C07D 471/04 514/234.5 |

FOREIGN PATENT DOCUMENTS

WO   WO-2014149164 A1 *   9/2014   ........... C07D 213/74

OTHER PUBLICATIONS

National Breast Cancer Foundation, accessed online, archived on Oct. 2, 2012. (Year: 2012).*
Sigma-Aldrich, MK2a Inhibitor—e CAS 41179-33-3, accessed on May 19, 2019, available online at: https://www.sigmaaldrich.com/catalog/product/mm/475863?lang=en&region=US. (Year: 2019).*
Davidson, W. et al.; Discovery and characterization of a substrate selective p38alpha inhibitor. Biochemistry 2004, vol. 43, No. 37, pp. 11658-11671.
Mourey, R. J. et al.; A benzothiophene inhibitor of mitogen-activated protein kinase-activated protein kinase 2 inhibits tumor necrosis factor alpha production and has oral anti-inflammatory efficacy in acute and chronic models of inflammation. Journal of Pharmacology and Experimental Therapeutics 2010, vol. 333, No. 3, pp. 797-807.
Qin, J. et al.; Discovery of a potent dihydrooxadiazole series of non-ATP-competitive MK (MAPKAPK2) inhibitors. ACS Medicinal Chemistry Letters 2012, vol. 3, pp. 100-105.
Siegel R, et al. Cancer statistics for Hispanics/Latinos, 2012. CA Cancer J Clin, 2012;62:283-298.
Dyson JK, Rutter MD. Colorectal cancer in inflammatory bowel disease: what is the real magnitude of the risk? World J Gastroenterol, 2012;18:3839-3848.
Feng YJ, Li YY. The role of p38 mitogen-activated protein kinase in the pathogenesis of inflammatory bowel disease. J Dig Dis, 2011;12:327-332.
Genovese MC. Inhibition of p38: has the fat lady sung? Arthritis Rheum, 2009;60:317-320.
Xu JJ, et al. Multiple effects of acetaminophen and p38 inhibitors: towards pathway toxicology. FEBS Lett, 2008;582:1276-1282.
Morris DL, et al. Acute lymphoid and gastrointestinal toxicity induced by selective p38alpha map kinase and map kinase-activated protein kinase-2 (MK2) inhibitors in the dog. Toxicol Pathol, 2010;38:606-618.

(Continued)

Primary Examiner — James H Alstrum-Acevedo
Assistant Examiner — Kaipeen E Yang
(74) *Attorney, Agent, or Firm* — Henry D. Coleman; R. Neil Sudol

(57) ABSTRACT

The present invention relates to the discovery that MK2 is highly expressed in cancer tissue and the inhibition of MK2 using an MK2 inhibitor represents a viable approach to the treatment of cancer, including drug resistant cancers, metastatic cancers and recurrent cancers. MK2 inhibitors as described herein may be used alone or in combination with an at least one additional anti-cancer agent for the treatment of cancer.

20 Claims, 34 Drawing Sheets

Specification includes a Sequence Listing.

(56) References Cited

OTHER PUBLICATIONS

Seimon TA, et al. Macrophage deficiency of p38alpha MAPK promotes apoptosis and plaque necrosis in advanced atherosclerotic lesions in mice. J Clin Invest, 2009;119:886-898.
Kotlyarov A, et al. Distinct cellular functions of MK2. Mol Cell Biol, 2002;22:4827-4835.
Garlanda C, et al. Increased susceptibility to colitis-associated cancer of mice lacking TIR8, an inhibitory member of the interleukin-1 receptor family. Cancer Res, 2007;67:6017-6021.
Grivennikov S, et al. IL-6 and Stat3 are required for survival of intestinal epithelial cells and development of colitis-associated cancer. Cancer Cell, 2009;15:103-113.
Mantovani A. Molecular pathways linking inflammation and cancer. Curr Mol Med, 2010;10:369-373.
Steinback EC, Plevy SE. The role of macrophages and dendritic cells in the initiation of inflammation in IBD. Inflamm Bowel Dis, 2014;20:166-175.
Zhang X, et al. the isolation and characterization of murine macrophages. Curr Protoc Immunol, 2008; Chapter 14.
Johansen C, et al. MK2 regulates the early stages of skin tumor promotion. Carcinogenesis, 2009;30:100-108.
Neufert C, et al. An inducible mouse model of colon carcinogenesis for the analysis of sporadic and inflammation driven tumor progression. Nat Protoc, 2007;2:1998-2004.
Guven ME, et al. The structural network of inflammation and cancer: merits and challenges. Semin Cancer Biol, 2013;23:243-251.
Strober W, Fuss IJ. Proinflammatory cytokines in the pathogenesis of inflammatory bowel diseases. Gastroenterology, 2011;40:1756-1767.
Ronkina N, et al. The mitogen-activated protein kinase (MAPK)-activated protein kinases MK2 and MK3 cooperate in stimulation of tumor necrosis factor biosynthesis and stabilization of p38 MAPK. Mol Cell Biol, 2007;27:170-181.
Tietz AB, et al. Gene deletion of MK2 inhibits TNF-alpha and IL-6 and protects against cerulean-induced pancreatitis. Am J Physiol Gastrointest Liver Physiol, 2006;290:G1298-G1306.
Randall KJ, et al. Explant culture of gastrointestinal tissue: a review of methods and applications. Cell Biol Toxicol, 2011;27:267-284.
Sheikh SZ, et al. IFN-gamma is a negative regulator of IL-23 in murine macrophages and experimental colitis. J Immunol, 2010;184:4069-4073.
Francisco-Cruz A, et al. Granulocyte-macrophage colony-stimulating factor: not just another haematopoietic growth factor. Med Oncol, 2014;31:774.
Zhang J, et al. CC chemokine ligand 2 (CCL2) promotes prostate cancer tumorigenesis and metastasis. Cytokine Growth Factor Rev, 2010;21:41-48.
Katoh H, et al. CXCR2-expressing myeloid-derived suppressor cells are essential to promote colitis-associated tumorigenesis. Cancer Cell, 2013;24:631-644.
Ichikawa M, et al. S100A8/A9 activate key genes and pathways in colon tumor progression. Mol Cancer Res, 2011;9:133-148.
Ray AL, et al. Inhibition of MK2 suppresses IL-1Beta, IL-6, and TNF-alpha-dependent colorectal cancer growth. International Journal of Cancer, 2017;Abstract.
Ray AL, et al. Abstract 2690: MK2 pathway blockade inhibits inflammatory cytokine production and colorectal cancer growth and invasion. AACR Annual Meeting, 2017.

\* cited by examiner

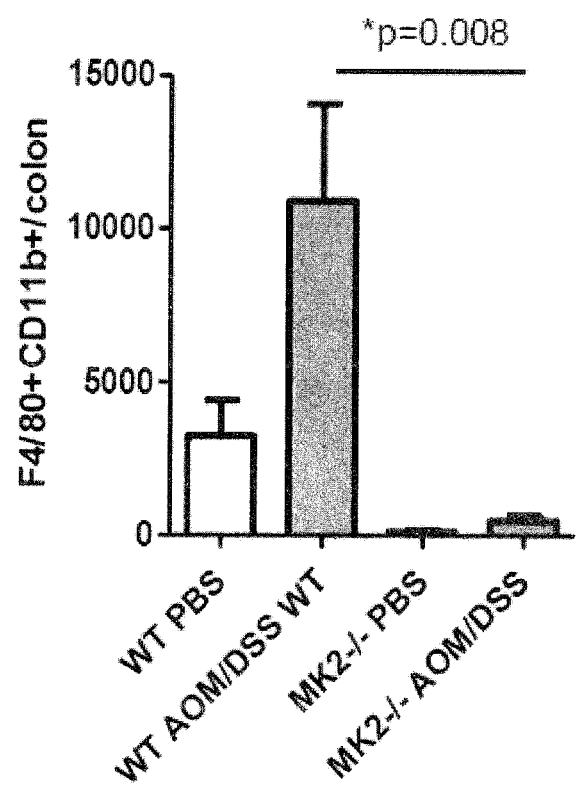

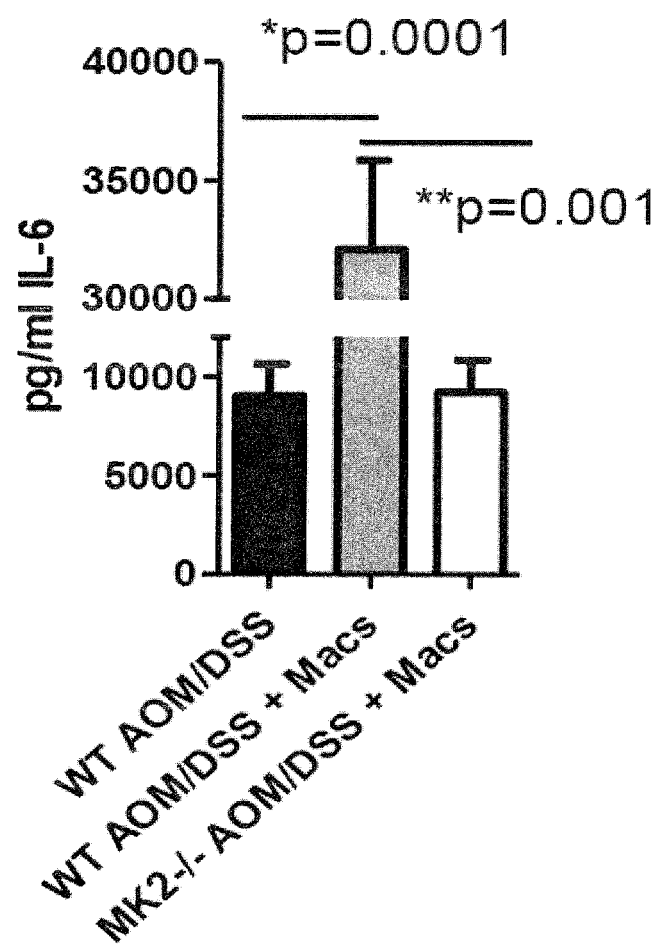

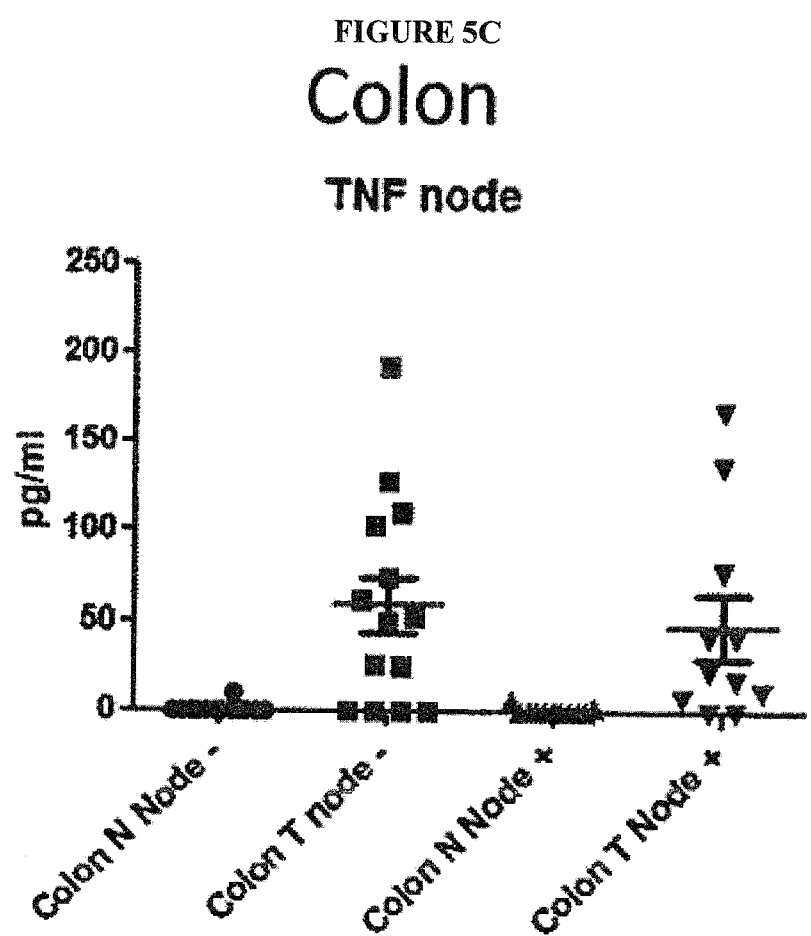

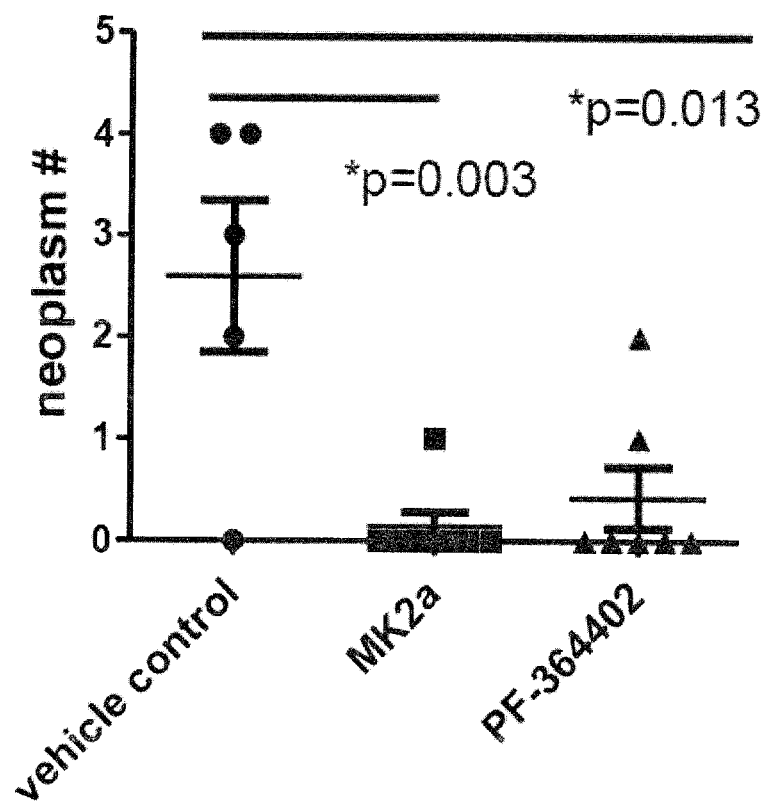

INHIBITION OF MK2 IN THE TREATMENT OF CANCER

CROSS-REFERENCE TO RELATED APPLICATIONS

This application claims the benefit of priority of U.S. Provisional Patent Application No. 62/041,491 filed 25 Aug. 2014, entitled "Inhibition of MK2 in the Treatment of GI Cancer", the entire contents of which are incorporated by reference herein.

STATEMENT REGARDING FEDERALLY SPONSORED RESEARCH OR DEVELOPMENT

This application is a United States national phase patent application based upon international patent application no. PCT/US2015/046238 filed Aug. 21, 2015, entitled "Inhibition of MK2 in the Treatment of Cancer", which claims the benefit of priority of U.S. Provisional Patent Application No. 62/041,491 filed 25 Aug. 2014, entitled "Inhibition of MK2 in the Treatment of GI Cancer", the entire contents of which two applications are incorporated by reference herein.

FIELD OF THE INVENTION

The present invention relates to the discovery that Map kinase activated protein kinase 2 (MK2) is highly expressed in cancer tissue and the inhibition of MK2 pathway with a MK2 pathway inhibitor represents a viable approach to the treatment of cancer, especially malignant tumors, including drug resistant cancers, metastatic cancers and recurrent cancers. MK2 inhibitors as described herein may be used alone or in combination with an at least one additional anti-cancer agent for the treatment of cancer. In addition, MK2 inhibitors may be used as a treatment for inflammatory bowel disease.

BACKGROUND AND DISCUSSION OF THE INVENTION

Gastric and colorectal cancers account for more than 600,000 deaths in the world each year. Gastric cancer is the fourth most prevalent cancer in the world and the second most common cause of cancer-related deaths (Torpy et al., 2010), while colon cancer is the second most common cancer in men and the third most common cancer in women (Jemal et aL, 2010). Chronic inflammation is one of the major risk factors associated with the development of both of these gastrointestinal cancers. There is a known link between gastric cancer and *Helicobacter pylori* infection, which is known to induce inflammatory cytokines in the stomach. Also, patients with chronic inflammatory bowel disease have an increased incidence of colon cancer that is approximately 18-19-fold compared to the general population (Gillen et al., 1994). Although a link between chronic inflammation and carcinogenesis is well established, the underlying mechanisms remain incompletely understood. Inflammatory mediators are thought to play a role in carcinogenesis by altering cell proliferation and inducing mutations that lead to the resistance of cancer cells to apoptosis. A greater understanding of the underlying mechanisms linking inflammation and gastrointestinal (GI) cancers is likely to lead to improved therapeutics.

MAP kinase-activated protein kinase 2 (MK2) is a downstream enzyme of the p38 pathway that is involved in multiple cellular processes such as inflammatory responses, gene expression regulation and cell proliferation. Furthermore, activation of MK2 leads to downstream activation of Heat Shock Protein 27 (HSP27), a protein known to inhibit apoptosis, as well as regulate cell development and differentiation. Based on these facts and that MK2 is upregulated in gastric and colon cancers, we hypothesize that MK2 small molecule inhibitors, will be a potential therapeutic modality for gastrointestinal tumors. We have recently demonstrated that mice lacking MK2 (MK2 knockout mice) do not develop gastric or colon tumors in established models of both tumor types. The significant results we have obtained could not have been predicted by the existing literature, and the hypothesis that MK2 inhibition will be an effective treatment in patients with gastrointestinal tumors is a new concept for which the present application has been filed.

BRIEF DESCRIPTION OF THE INVENTION

The inventors have discovered that MAP kinase-activated protein kinase 2 (MK2) is upregulated in cancer tissue, especially cancerous gastrointestinal tissue and because of this excessive upregulation, is an excellent target for the inhibition and/or treatment of cancer using a MK2 inhibitor. From these studies the inventors have determined that MK2 inhibitors are particularly potent anti-cancer compounds and may be used alone or in combination with other anticancer agents and/or therapies for the treatment and/or inhibition (including the prolongation of remission) of the growth, elaboration, metastasis and/or recurrence of cancer in a patient in need, especially including gastrointestinal cancer.

The present invention provides the bases for novel and clinically-significant therapies that supplement and complement known anti-cancer regimens.

In a first embodiment, the present invention is directed to a method of treating cancer in a patient or subject in need comprising co-administering to the patient subject a pharmaceutically effective amount of:

(a) one or more compounds which is a MK2 inhibitor; optionally, (b) at least one additional anticancer agent, wherein the administration of the MK2 inhibitor and optional additional anticancer agent is optionally combined with radiation or alternative therapy of said cancer.

In certain embodiments according to the present invention the MK2 inhibitor(s) is administered to the cancer patient with at least one additional anticancer agent to provide a synergistic effect in the treatment of cancer.

In certain embodiments, the MK2 inhibitor is administered in effective amounts alone or in combination with an effective amount of an additional anticancer agent as otherwise described herein for the treatment of cancer, which treatment method may be optionally combined with radiation or an alternative therapy as described herein.

Related pharmaceutical formulations pursuant to the present invention are also provided.

In a particular embodiment, the present invention provides a method of treating a subject who suffers from a cancer selected from the group consisting of GI cancers, including stomach cancer, esophageal cancer (EC), pancreatic cancer and colorectal cancers, the method comprising co-administering to the subject a pharmaceutically-effective amount of:

(a) one or more MK2 inhibitor compounds;

(b) one or more anticancer agents (often, a chemotherapeutic agent), wherein the administration of said MK2 inhibitor(s) and said additional anticancer agent is optionally further combined with radiation or alternative therapy of said cancer, especially gastrointestinal cancer.

In certain embodiments, the subject is treated concomitantly by radiotherapy and/or other alternative therapy and the MK2 inhibitor(s) and optionally an additional anticancer agent wherein the MK2 inhibitor(s) and optional additional anticancer agent are administered to the subject prior to or during radiation therapy.

As described, in certain embodiments, the subject is also treated concomitantly by additional anticancer agents as otherwise described herein, including chemotherapeutic agents such as agents which are DNA damaging agents, including such agents as paclitaxel and docetaxel, platinum-based antineoplastics (e.g. cisplatin, carboplatin, oxaliplatin, satraplatin, picoplatin, Nedaplatin, Triplatin, and Lipoplatin). In certain additional embodiments, further treatment of a cancer using hormonal therapy, proton therapy, cryosurgery, and/or high intensity focused ultrasound (HIFU) is used, depending upon clinical assessments and treatment goals. In addition; treatment methods pursuant to the present application may include antibody therapies and/or tyrosine kinase inhibitors.

In certain embodiments, the subject suffers from a treatment-resistant cancer, including a metastatic and/or recurrent cancer, such as stomach cancer, esophageal cancer (EC), pancreatic cancer and colorectal cancers, among others, as described herein.

In a further embodiment, the invention provides a method of treating a subject who suffers from cancer (especially including a recurrent cancer) wherein the cancer has developed resistance to one or more cancer agents, the method comprising administering an effective amount of
(a) one or more MK2 inhibitors; and optionally
(b) one or more additional anticancer agent to which the cells have not become resistant; and/or
(c) at least one anticancer agent (e.g., a chemotherapeutic agent such as a DNA damaging agent), wherein the method may be combined further with radiation therapy or alternative therapy (e.g., hormonal therapy, proton therapy, cryosurgery, and/or high intensity focused ultrasound (HIFU), radiofrequency ablation, microwave ablation, transarterial therapies such as radioembolization with Y90 or bland embolization and chemoembolization (for liver cancer).

In still another embodiment, the present invention relates to a method to treat inflammatory bowel disease comprising administering to a patient in need an effective amount of at least one MK2 inhibitor as disclosed herein, optionally in combination with another agent effective for treating inflammatory bowel disease, including a 5-Aminosalicylic acid derivatives (eg, sulfasalazine, mesalamine, balsalazide, olsalazine); antibiotics (eg, metronidazole, ciprofloxacin, rifaximin); corticosteroid agents (eg, hydrocortisone, prednisone, methylprednisolone, prednisolone, budesonide, dexamethasone); immunosuppressant agents (eg, azathioprine, 6-mercaptopurine, methotrexate, cyclosporine); tumor necrosis factor inhibitors (eg, infliximab, adalimumab, certolizumab pegol); monoclonal antibodies (eg, natalizumab); H2-receptor antagonists (eg, cimetidine, ranitidine, famotidine, nizatidine); proton pump inhibitors (eg, omeprazole, lansoprazole, esomeprazole magnesium, rabeprazole sodium, pantoprazole), antidiarrheal agents (eg, diphenoxylate and atropine, loperamide, cholestyramine) and anticholinergic antispasmodic agents (eg, dicyclomine, hyoscyamine), among others.

Pharmaceutical formulations that are useful in the treatment of a variety of cancers and inflammatory disorders are also provided. These formulations comprise (a) one or more elements or compounds selected from the group consisting of at least one MK-2 inhibitor as set forth herein, and optionally at least one additional anticancer agent and/or an agent effective for treating inflammatory bowel disease (e.g., a 5-Aminosalicylic acid derivative (eg, sulfasalazine, mesalamine, balsalazide, olsalazine); antibiotic (eg, metronidazole, ciprofloxacin, rifaximin); corticosteroid agent (eg, hydrocortisone, prednisone, methylprednisolone, prednisolone, budesonide, dexamethasone); immunosuppressant agent (eg, azathioprine, 6-mercaptopurine, methotrexate, cyclosporine); tumor necrosis factor inhibitor (eg, infliximab, adalimumab, certolizumab pegol); monoclonal antibodies (eg, natalizumab); H2-receptor antagonist (eg, cimetidine, ranitidine, famotidine, nizatidine); proton pump inhibitor (eg, omeprazole, lansoprazole, esomeprazole magnesium, rabeprazole sodium, pantoprazole), antidiarrheal agent (eg, diphenoxylate and atropine, loperamide, cholestyramine) and anticholinergic antispasmodic agent (eg, dicyclomine, hyoscyamine), among others, and a pharmaceutically-acceptable additive, carrier and/or excipient.

In certain embodiments, by combining at least one MK-2 inhibitor with additional anticancer agents and further optionally, radiation or other alternative anticancer therapy, the methods and formulations described herein prove particularly effective in treating a wide variety of cancers that have been previously associated with high rates of remission, but poor long-term survival, especially when combined with a chemotherapy agent and optionally, radiation and/or other alternative anticancer therapy (e.g., hormonal therapy, proton therapy, cryosurgery, and/or high intensity focused ultrasound (HIFU), radiofrequency ablation, microwave ablation, transarterial therapies such as radioembolization with Y90 or bland embolization and chemoembolization (for liver cancer)).

These and other aspects of the invention are described further in the Detailed Description of the Invention.

BRIEF DESCRIPTION OF THE FIGURES

FIG. 4A shows that human colon cancer primary tumors have increased gene expression of MK2 and downstream Hsp27. Expression is significantly higher in samples from patients with node positive disease. FIG. 4B shows that human tissues from *H. pylori* infected individuals have increased MK2 gene expression as gastric tumor samples with a history of *H. pylori* infection.

FIG. 5A-D are graphs showing that human colon and gastric cancers have increased MK2 downstream cytokine expression associated with lymph node metastasis.

FIG. 7A is pursuant to a Azoxymethance (AOM)/Dextran sulfate sodium (DSS) model of colon cancer. FIG. 7B is pursuant to a N-methyl-N-nitrosurea (MNU)/*Helicobacter pylori* (Hp) model of gastric cancer.

FIG. 8B is pursuant to an MK2 knockout mice have decreased production of MK2 downstream cytokines in established models of gastric and colon cancer. FIG. 8C is pursuant to an MNU/Hp model of gastric cancer.

FIG. 10 is a graph showing that AOM/DSS exposed mice treated with MK2 inhibitors regresses neoplasms. AOM/DSS exposed mice treated with MK2a inhibitor or PF-3644022 Inhibitor three times a week for three weeks have significantly less neoplasms.

DETAILED DESCRIPTION OF THE INVENTION

Figure 1A:
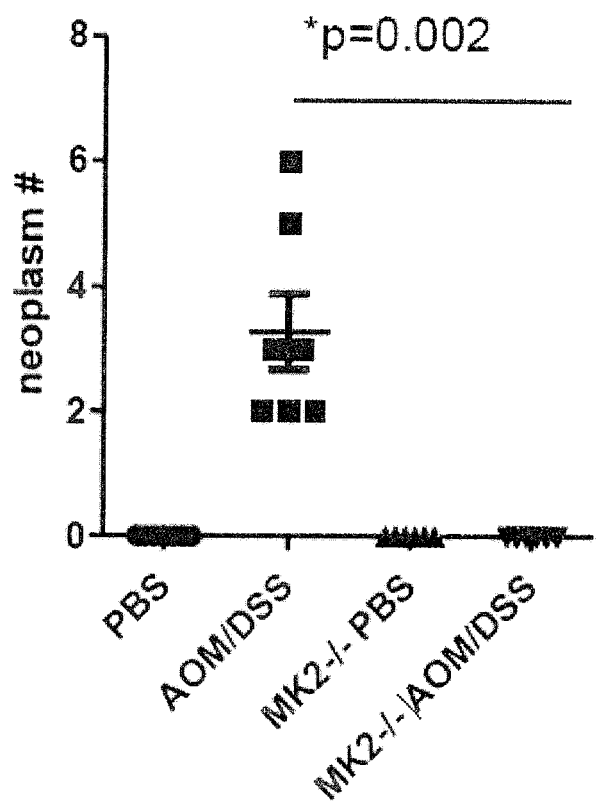
FIG. 1. MK2$^{-/-}$ mice exposed to AOM/DSS do not develop neoplasms and have substantially decreased cytokine production compared to WT mice. AOM/DSS treated mice develop A) multiple neoplasms, while MK2$^{-/-}$ mice do not. H&E staining indicates that B) AOM/DSS treated WT mice developed defined neoplasms with dysplastic proliferation of the colonic epithelium compared to C) architectural disarray of mucosal tissue consistent with chronic injury from multiple DSS treatments, while D) AOM/DSS treated MK2$^{-/-}$ mice displayed no visible signs of dysplasia or mucosal damage. AOM/DSS treated MK2$^{-/-}$ mice have significantly decreased E) IL-1α, F) IL-1β, G) IL-6, and H) TNF-α in organ culture supernatants compared to WT mice by multiplex bead array. N=7 for WT mice and 8 for MK2$^{-/-}$ mice in duplicate experiments.

The following terms are used throughout the specification to describe the present invention. Where a term is not given a specific definition herein, that term is to be given the same meaning as understood by those of ordinary skill in the art. The definitions given to the disease states or conditions which may be treated using one or more of the compounds according to the present invention are those which are generally known in the art.

It is noted that, as used in this specification and the appended claims, the singular forms "a," "an," and "the," include plural referents unless expressly and unequivocally limited to one referent. Thus, for example, reference to "a compound" includes two or more different compound. As used herein, the term "include" and its grammatical variants are intended to be non-limiting, such that recitation of items in a list is not to the exclusion of other like items that can be substituted or other items that can be added to the listed items.

The term "patient" or "subject" is used throughout the specification to describe an animal, preferably a human, to whom treatment, including prophylactic treatment, with the compositions according to the present invention is provided (a patient or subject in need). For treatment of those infections, conditions or disease states which are specific for a specific animal such as a human patient, the term patient refers to that specific animal. In many instances, diagnostic methods are applied to patients or subjects who are suspected of having cancer or who have cancer or a inflammatory disorder and the diagnostic method is used to assess the severity of the disease state or disorder.

The term "compound" is used herein to refer to any specific chemical compound disclosed herein and in particular, a MK2 inhibitor, anticancer agent or other agent used in the present invention such as an agent effective in the treatment of inflammatory bowel disease. Within its use in context, the term generally refers to a single small molecule as disclosed herein, but in certain instances may also refer to other forms of the compound, including enantiomers, racemic mixtures and other compositions especially including polypeptides, antibodies and poly- and monoclonal antibodies. The term compound includes active metabolites of compounds and/or pharmaceutically acceptable salts thereof.

The term "effective amount" is used throughout the specification to describe concentrations or amounts of formulations or other components which are used in amounts, within the context of their use, to produce an intended effect according to the present invention, for example to inhibit MK2 and the effects of MK2, to kill cells and/or damage DNA as a chemotherapy agent or by exposure to radiation or other alternative therapy as described herein. The formulations or component(s) may be used to produce a favorable change in a disease or condition treated, whether that change is a remission of effects of a disease state or condition, a favorable physiological result, a reversal or attenuation of a disease state or condition treated, the prevention or the reduction in the likelihood of a condition or disease-state occurring, depending upon the disease or condition treated. Where formulations are used in combination, each of the formulations is used in an effective amount, wherein an effective amount may include a synergistic amount. The amount of formulation used in the present invention may vary according to the nature of the formulation, the age and weight of the patient and numerous other factors which may influence the bioavailability and pharmacokinetics of the formulation, the amount of formulation which is administered to a patient generally ranges from less than about 0.001 mg/kg to about 50 mg/kg or more, about 0.1 mg/kg to about 7.5 mg/kg, about 0.5 mg/kg to about 25 mg/kg, about 0.1 to about 15 mg/kg, about 1 mg to about 10 mg/kg per day and otherwise described herein. The person of ordinary skill may easily recognize variations in dosage schedules or amounts to be made during the course of therapy.

"MK2 inhibitors" include any compound or its pharmaceutically acceptable salt, alternative pharmaceutically acceptable salt, enantiomer, isomer, solvate (including hydrate) or polymorph which is capable of inhibiting MK2. Preferred MK2 inhibitors include compounds such as BIO-475863 (MK2a inhibitor, available from Calbiochem), (10R)-9,10,11,12-Tetrahydro-10-methyl-3-(6-methyl-3- pyridinyl)-8H-[1,4]diazepino[5',6':4,5]thieno[3,2-f]quinolin-8-one (PF3644022, from R&D Systems, Inc.), as well as MK2 III and MK2 IV (available from both EMD Millipore and Sigma Aldrich), among others. These compounds have the following chemical structures:

Inhibitor 1 BIO-475863 (CAS-41179-33-3):

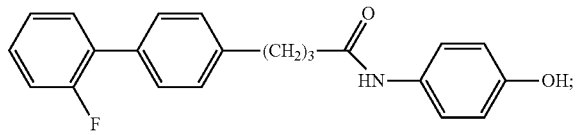

Inhibitor 2 PF-364402 (commercially available as the hydrate):

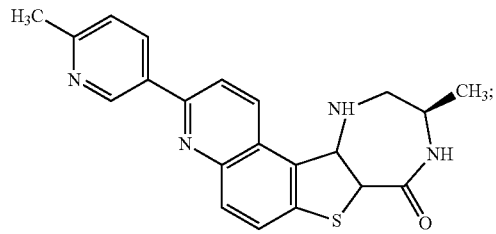

Inhibitor 3 (MK2 III) preferably, as monohydrate

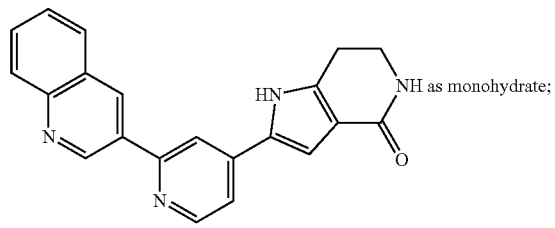

Inhibitor 4 MK2 IV (preferably, as HCl salt):

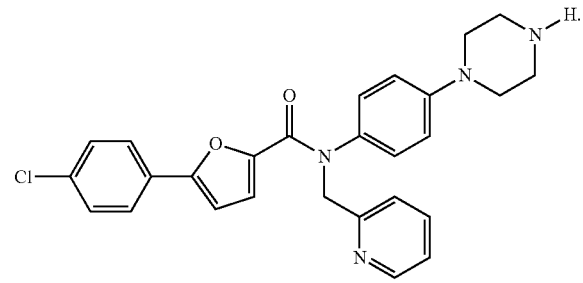

Another MK2 inhibitor for use in the present invention is MK2i, which is a polypeptide having the peptide sequence WLRRIKAWLRRIKALNRQLGVAA (SEQ ID NO:1), which may be used alone or in combination with other MK2 inhibitors as described herein, optionally in combination with at least one additional anticancer agent and/or an additional agent effective for treating inflammatory bowel disease as described herein. MK2i may be used as its pharmaceutically acceptable salt. In certain embodiments, the compound staurosporine or UCN-01, available from a number of chemical suppliers may also be used.

These compounds, among others, may be used to inhibit MK2 and consequently, treat cancer, especially including gastrointestinal cancer, including metastatic and recurrent cancer, through the inhibition of the growth, elaboration and metastasis and reduce the likelihood of metastasis and/or recurrence of a cancer which has gone into remission. One or more of these compounds may be used alone or in combination with at least one additional anticancer agent, and optionally radiation and other anticancer therapy in the treatment of cancer. In certain embodiments, further treatment of a cancer using hormonal therapy, proton therapy, cryosurgery, and/or high intensity focused ultrasound (HIFU), radiofrequency ablation, microwave ablation, transarterial therapies such as radioembolization with Y90 or bland embolization and chemoembolization (for liver cancer) is used, depending upon clinical assessments and treatment goals.

The term "prophylactic" is used to describe the use of a formulation described herein which reduces the likelihood of an occurrence of a condition or disease state in a patient or subject. The term "reducing the likelihood" refers to the fact that in a given population of patients, the present invention may be used to reduce the likelihood of an occurrence, recurrence or metastasis of disease in one or more patients within that population of all patients, rather than prevent, in all patients, the occurrence, recurrence or metastasis of a disease state.

The term "pharmaceutically acceptable" refers to a salt form or other derivative (such as an active metabolite or prodrug form) of the present compounds or a carrier, additive or excipient which is not unacceptably toxic to the subject to which it is administered.

"Treat", "treating", and "treatment", etc., as used herein, refer to any action providing a benefit to a patient at risk for or afflicted with a disease, including improvement in the condition through lessening or suppression of at least one symptom, delay in progression of the disease, prevention or delay in the onset of the disease, etc. Treatment, as used herein, encompasses both prophylactic and therapeutic treatment.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Cancers generally show partial or complete lack of structural organization and functional coordination with the normal tissue and most invade surrounding tissues, metastasize to several sites, and are likely to recur after attempted removal (recurrent cancer) and to cause the death of the patient unless adequately treated.

As used herein, the term cancer is used to describe all cancerous disease states applicable to treatment according to the present invention and embraces or encompasses the pathological process associated with all virtually all epithelial cancers, including carcinomas, malignant hematogenous, ascitic and solid tumors. Examples of cancers which may be treated using methods according to the present invention include, without limitation, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; leukemias (various); benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, glioblastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas. See, for example, The Merck Manual of Diagnosis and Therapy, 17.sup.th ed. (Whitehouse Station, N.J.: Merck Research Laboratories, 1999) 973-74, 976, 986, 988, 991).

In addition to the treatment of ectopic cancers, the present invention, particularly where the inhibitor is an MK2 inhibitor, is often used to treat gastrointestinal cancers, especially stomach cancer, colon cancer, rectal cancer (colorectal), esophageal, pancreatic and throat cancer, as well as in certain instances, liver cancer and pancreatic cancer.

In addition to the treatment of ectopic cancers as described above, the present invention also may be used preferably to treat eutopic cancers such as choriocarcinoma, testicular choriocarcinoma, non-seminomatous germ cell testicular cancer, placental cancer (trophoblastic tumor) and embryonal cancer, among others.

The term "neoplasia" refers to the uncontrolled and progressive multiplication of tumor cells, under conditions that would not elicit, or would cause cessation of, multiplication of normal cells. Neoplasia results in a "neoplasm", which is defined herein to mean any new and abnormal growth, particularly a new growth of tissue, in which the growth of cells is uncontrolled and progressive. Thus, neoplasia includes "cancer", which herein refers to a proliferation of tumor cells having the unique trait of loss of normal controls, resulting in unregulated growth, lack of differentiation, local tissue invasion, and/or metastasis.

As used herein, neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms are distinguished from benign neoplasms in that the former show a greater degree of anaplasia, or loss of differentiation and orientation of cells, and have the properties of invasion and metastasis. Examples of (many of which are identified above) include neoplasms or neoplasias from which the target cell of the present invention may be derived include, without limitation, carcinomas (e.g., squamous-cell carcinomas, basal cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas (Beers and Berkow (eds.), The Merck Manual of Diagnosis and Therapy, 17.sup.th ed. (Whitehouse Station, N.J.: Merck Research Laboratories, 1999) 973-74, 976, 986, 988, 991.

The term "anticancer agent" or "additional anticancer agent" shall mean chemotherapeutic agents including such as an agent selected from the group consisting of microtubule-stabilizing agents, microtubule-disruptor agents, alkylating agents, antimetabolites, epidphyllotoxins, antineoplastic enzymes, topoisomerase inhibitors, inhibitors of cell cycle progression, and platinum coordination complexes. These may be selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolyl]-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-NH$_2$ acetate [$C_{59}H_{84}N_{18}Oi_4$-$(C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, among others.

The term "DNA damaging agent" refers to a chemotherapeutic agent which may be used as an additional anticancer agent in the methods of the present invention, which specifically damages DNA of a cancer cell either directly or indirectly in its actions. Many chemotherapy agents are considered DNA damaging agents. Preferred agents include alkylating agents, including nitrogen mustards: such as mechlorethamine (nitrogen mustard), chlorambucil, cyclophosphamide (Cytoxan®), ifosfamide, and melphalan; Nitrosoureas, including streptozocin, carmustine (BCNU), and lomustine; Alkyl sulfonates, including busulfan; Triazines, including dacarbazine (DTIC) and temozolomide (Temodar®); Ethylenimines, including thiotepa and altretamine (hexamethylmelamine); Platinum drugs, including cisplatin, carboplatin and oxalaplatin; Antimetabolites including fluorouracil (5-FU), 6-mercaptopurine (6-MP), Capecitabine (Xeloda®), Cladribine, Clofarabine, Cytarabine (Ara-C®), Floxuridine, Fludarabine, Gemcitabine (Gemzar®), Hydroxyurea, Methotrexate, Pemetrexed (Alimta®), Pentostatin, Thioguanine; Anti-tumor antibiotics including Anthracyclines, such as Daunorubicin, Doxorubicin (Adriamycin®), Epirubicin, Idarubicin and non-anthracycline antibioitics Actinomycin-D, Bleomycin and Mitomycin-C; Topoisomerase inhibitors including topotecan and irinotecan (CPT-11), etoposide (VP-16), teniposide and Mitoxantrone; Mitotic inhibitors, including Taxanes: paclitaxel (Taxol®) and docetaxel (Taxotere®); Epothilones, including ixabepilone (Ixempra®); Vinca alkaloids, including vinblastine (Velban®), vincristine (Oncovin®), and vinorelbine (Navelbine), Estramustine (Emcyt®); and Targeted therapies including imatinib (Gleevec®), gefitinib (Iressa®), sunitinib (Sutent®) and bortezomib (Velcade®), among others.

The terms "radiotherapy" and "radiation therapy" are used interchangeably and describe therapy for cancer, especially including prostate cancer, which may be used in conjunction with certain MK2 inhibitor compounds in combination with other agents, including those having radiation sensitization activity. Radiation therapy uses high doses of radiation, such as X-rays or other energy sources such as radioisotopes (gamma, beta or alpha emitters), to destroy cancer cells. The radiation damages the genetic material of the cells so that they cannot grow. Although radiation damages normal cells as well as cancer cells, the normal cells can repair themselves and function, while the cancer cells cannot.

Radiation therapy may be used in combination with the presently claimed compounds, alone or in combination with additional anticancer compounds as otherwise disclosed herein, depending on the cancer to be treated, and consequently, the cancer cells' ability to repair damage done by the radiation, thus potentiating radiation therapy. Radiation therapy is most effective in treating cancers that have not spread (metastasized). But it also may be used if the cancer has spread to nearby tissue. Radiation is sometimes used after surgery to destroy any remaining cancer cells and to relieve pain from metastatic cancer.

Radiation is delivered in one of two ways: External-beam radiation therapy and brachytherapy. External-beam radiation therapy uses a large machine to aim a beam of radiation at the tumor. After the area of cancer is identified, an ink tattoo no bigger than a pencil tip is placed on the skin of the subject so that the radiation beam can be aimed at the same spot for each treatment. This helps focus the beam on the cancer to protect nearby healthy tissue from the radiation. External radiation treatments usually are done 5 days a week for 4 to 8 weeks or more. If cancer has spread, shorter periods of treatment may be given to specific areas to relieve pain.

There are basically three types of external radiation therapy: conformal radiotherapy (3D-CRT), intensity-modulation radiation therapy (IMRT) and proton therapy. Conformal radiotherapy uses a three-dimensional planning system to target a strong dose of radiation to the cancer. This helps to protect healthy tissue from radiation. Intensity-modulated radiation therapy uses a carefully adjusted amount of radiation. This protects healthy tissues more than conformal radiotherapy does. Proton therapy uses a different type of energy (protons) than X-rays. This approach allows a higher amount of specifically directed radiation, which protects nearby healthy tissues the most. Sometimes proton therapy is combined with X-ray therapy.

Brachytherapy, or internal radiation therapy, uses dozens of tiny seeds that contain radioactive material. It may be used preferably to treat early-stage prostate and other cancer which is localized. Needles are used to insert the seeds through the skin into tissue, most often the prostate. The surgeon uses ultrasound to locate the tissue and guide the needles. As the needles are pulled out, the seeds are left in place. The seeds release radiation for weeks or months, after which they are no longer radioactive. The radiation in the seeds can't be aimed as accurately as external beams, but they are less likely to damage normal tissue. After the seeds have lost their radioactivity, they become harmless and can stay in place.

Radiation therapy may combine brachytherapy with low-dose external radiation. In other cases, treatment combines surgery with external radiation. In the present invention, compounds which are otherwise claimed may be used as radiation sensitizers to enhance or potentiate the effect of radiation by inhibiting the ability of the cancer tissue to repair the damage done by the radiation therapy.

Other alternative therapies which can be used in combination with MK 2 inhibitors and optionally radiation therapy, include for example hormonal therapy, proton therapy, cryosurgery, and/or high intensity focused ultrasound (HIFU), radiofrequency ablation, microwave ablation, transarterial therapies such as radioembolization with Y90 or bland embolization and chemoembolization (for liver cancer).

Formulations of the invention may include a pharmaceutically acceptable diluent, carrier, solubilizer, emulsifier, preservative and/or adjuvant. Acceptable formulation materials preferably are nontoxic to recipients at the dosages and concentrations employed. The pharmaceutical formulations may contain materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides, disaccharides, and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, polyethylene glycol (PEG), sorbitan esters, polysorbates such as polysorbate 20 and polysorbate 80, Triton, trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants. See, for example, REMINGTON'S PHARMACEUTICAL SCIENCES, 18.sup.th Edition, (A. R. Gennaro, ed.), 1990, Mack Publishing Company.

Optimal pharmaceutical formulations can be determined by one skilled in the art depending upon, for example, the intended route of administration, delivery format and desired dosage. See, for example, REMINGTON'S PHARMACEUTICAL SCIENCES, Id. Such formulations may influence the physical state, stability, rate of in vivo release and rate of in vivo clearance of the antibodies of the invention.

Primary vehicles or carriers in a pharmaceutical formulation can include, but are not limited to, water for injection, physiological saline solution or artificial cerebrospinal fluid, possibly supplemented with other materials common in compositions for parenteral administration. Neutral buffered saline or saline mixed with serum albumin are further exemplary vehicles. Pharmaceutical formulations can comprise Tris buffer of about pH 7.0-8.5, or acetate buffer of about pH 4.0-5.5, which may further include sorbitol or a suitable substitute. Pharmaceutical formulations of the invention may be prepared for storage by mixing the selected composition having the desired degree of purity with optional formulation agents (REMINGTON'S PHARMACEUTICAL SCIENCES, Id.) in the form of a lyophilized cake or an aqueous solution. Further, the formulations may be formulated as a lyophilizate using appropriate excipients such as sucrose.

Formulation components are present in concentrations that are acceptable to the site of administration. Buffers are advantageously used to maintain the composition at physiological pH or at a slightly lower pH, typically within a pH range of from about 5 to about 8.

The pharmaceutical formulations of the invention can be delivered parenterally. When parenteral administration is contemplated, the therapeutic formulations for use in this invention may be in the form of a pyrogen-free, parenterally acceptable aqueous solution. Preparation involves the formulation of the desired immunomicelle, which may provide controlled or sustained release of the product which may then be delivered via a depot injection. Formulation with hyaluronic acid has the effect of promoting sustained duration in the circulation.

Formulations may be formulated for inhalation. In these embodiments, a stealth immunomicelle formulation is formulated as a dry powder for inhalation, or inhalation solutions may also be formulated with a propellant for aerosol delivery, such as by nebulization. Pulmonary administration is further described in PCT Application No. PCT/US94/001875, which describes pulmonary delivery of chemically modified proteins and is incorporated by reference.

Formulations of the invention can be delivered through the digestive tract, such as orally. The preparation of such pharmaceutically acceptable compositions is within the skill of the art. Formulations disclosed herein that are administered in this fashion may be formulated with or without those carriers customarily used in the compounding of solid dosage forms such as tablets and capsules. A capsule may be designed to release the active portion of the formulation at the point in the gastrointestinal tract when bioavailability is maximized and pre-systemic degradation is minimized Additional agents can be included to facilitate absorption. Diluents, flavorings, low melting point waxes, vegetable oils, lubricants, suspending agents, tablet disintegrating agents, and binders may also be employed.

A formulation may involve an effective quantity of a microparticle containing formulation as disclosed herein in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

The pharmaceutical composition to be used for in vivo administration typically is sterile. In certain embodiments, this may be accomplished by filtration through sterile filtration membranes. In certain embodiments, where the composition is lyophilized, sterilization using this method may be conducted either prior to or following lyophilization and reconstitution. In certain embodiments, the composition for parenteral administration may be stored in lyophilized form or in a solution. In certain embodiments, parenteral compositions generally are placed into a container having a sterile access port, for example, an intravenous solution bag or vial having a stopper pierceable by a hypodermic injection needle.

Once the formulation of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

Administration routes for formulations of the invention include orally, through injection by intravenous, intraperitoneal, intracerebral (intra-parenchymal), intracerebroventricular, intramuscular, intra-ocular, intraarterial, intraportal, intrathecal or intralesional routes; by sustained release systems or by implantation devices, transdermally or topically among other routes of administration, including bucally or via suppository. The pharmaceutical formulations may be administered by bolus injection or continuously by infusion, or by implantation device. The pharmaceutical formulations also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

MK2 Inhibitor

Preferred methods of treatment and pharmaceutical formulations include the following.

In one embodiment, the invention provides a method of treating a subject who suffers from a cancer (any cancer as otherwise disclosed herein), preferably a gastrointestinal or other cancer selected from the group consisting of stomach cancer, colon cancer, rectal cancer, esophageal cancer, pancreatic cancer and throat cancer, the method comprising co-administering to the subject a pharmaceutically-effective amount of:

(a) one or more elements or compounds which is a MK2 inhibitor;
(b) optionally, one or more additional anticancer agents, including a chemotherapy agent (preferably, at least one DNA-damaging agent); and
(c) optionally, employing radiation and/or other alternative therapy.

In a preferred embodiment, the subject is treated concomitantly by radiotherapy and the one or more MK2 inhibitor compounds is combined with an agent are administered to the subject as a radiosensitizer prior to or during radiotherapy, optionally in combination with at least one additional anticancer agent as otherwise disclosed herein.

In certain embodiments, the subject suffers from a treatment-resistant cancer selected from the group consisting of stomach cancer, colon cancer, rectal cancer (colorectal cancer), esophageal cancer, pancreatic cancer and throat cancer, including recurrent cancer.

Preferably, the MK2 inhibitor agent is selected from the group consisting of PF-3644022, BIO-475863, MK2 III, MK2 IV and mixtures thereof. PF-3644022 is available for research use from Sigma Aldrich, developed by Pfizer; specifications of PF-3644022 are set forth at http://www.sigmaaldrich.com/catalog/product/sigma/pz0188?lang=en®ion-US. The MK2a inhibitor BIO-475863 is available from EMD Millipore and specifications can be found at the website emdmillipore.com/US/en/product/MK2a-Inhibitor CAS-41179-33-3-Calbiochem, EMD BIO-475863. The MK2 inhibitor agent may alternatively take the form of MK2 III or MK2 IV—available from both EMD Millipore and Sigma Aldrich as described hereinabove. Pharmaceutically acceptable salts, alternative pharmaceutically acceptable salts, enantiomers, solvates and polymorphs are other forms of MK2 inhibitors which are useful in the present invention.

In further embodiments, the MK2 inhibitor may be combined with at least one additional anticancer agent including preferably at least one additional PARP inhibitor selected from the group consisting of arsenic trioxide (ATO), NU1025; 3-aminobenzamide; 4-amino-1,8-naphthalimide; 1,5-isoquinolinediol; 6(5H)-phenanthriddinone; 1,3,4,5-tetrahydrobenzo(c)(1,6)- and (c)(1,7)-naphthyridin-6 ones; adenosine substituted 2,3-dihydro-1H-isoindol-1-ones; AG14361; AG014699; 2-(4-chlorophenyl)-5-quinoxalinecarboxamide; 5-chloro-2-[3-(4-phenyl-3,6-dihydro-1 (2H)-pyridinyl)propyl]-4(3H)-quinazolinone; isoindolinone derivative INO-1001; 4-hydroxyquinazoline; 2-[3-[4-(4-chlorophenyl) 1-piperazinyl]propyl]-4-3(4)-quinazolinone; 1,5-dihydroxyisoquinoline (DHIQ); 3,4-dihydro-5 [4-(1-piperidinyl)(butoxy)-1(2H)-isoquinolone; CEP-6800; GB-15427; PJ34; DPQ; BS-201; AZD2281 (Olaparib); BS401; CHP101; CHP102; INH2BP; BSI201; BSI401; TIQ-A; an imidazobenzodiazepine; 8-hydroxy-2-methylquinazolinone (NU1025), CEP 9722, MK 4827, LT-673; 3-aminobenzamide; Olaparib (AZD2281; ABT-888 (Veliparib); BSI-201 (Iniparib); Rucaparib (AG-014699); INO-1001; A-966492; PJ-34; and the PARP1 inhibitors described in U.S. patent application Ser. No. 12/576,410.

The subject treated in the embodiment of the preceding paragraph may suffer from one or more cancers selected from the group consisting of gastrointestinal cancer, stomach cancer, colon cancer, rectal cancer, esophageal cancer, throat cancer and pancreatic cancer as this therapeutic approach is particularly suited for these cancers.

Another preferred embodiment provides a method of treating a subject who suffers from a solid tumor, the method comprising co-administering to the subject a pharmaceutically-effective amount of:

(a) one or more MK2 inhibitors; and
(b) optionally, at least one additional anticancer agent. This method may also be used in combination with radiation and/or other alternative therapy (e.g., hormonal therapy, proton therapy, cryosurgery, and/or high intensity focused ultrasound (HIFU), radiofrequency ablation, microwave ablation, transarterial therapies such as radioembolization with Y90 or bland embolization and chemoembolization (for liver cancer)).

These and other aspects of the invention are illustrated further in the following non-limiting Examples.

EXAMPLES

Materials and Methods:

Mice: C57Bl/6 mice from Harlan Laboratories and the MK2$^{-/-tm1Mgl}$ (8) mouse strain were bred under pathogen free conditions. Animal procedures were approved by the UNM IACUC. Azoxymethane (AOM), (Sigma Aldrich, St. Louis, Mo.) was injected JP into 6-8 week old female mice at 12.5 mg/kg. Dextran Sodium Sulfate (DSS), (MP Biomedicals, MW 36,000-50,000) was added to drinking water at 2.5% at days 5 and 26 and at 2.0% at day 47, 2.0% for 5 days sacrificed at day 80. Control mice received PBS IP and no DSS in water. Mouse Colon Supernatants: 8 mg (±0.5 mg) of cleaned colon tissues were incubated in complete RPMI with antibiotics for 12 hours. Supernatants were analyzed for cytokines by Luminex bead array (Millipore, Billerica, Mass.) according to manufacturer's instructions.

Flow Cytometry: Mouse colon tissues were treated with collagenase (I, II, and IV, Sigma Aldrich) and dispersed using the gentleMACs tissue dissociator (Miltenyi Biotech, Cologne, Germany). Cell suspensions were incubated overnight in media before staining for flow cytometry according to standard Biolegend protocols (Biolegend, San Diego, Calif.). Macrophages were stained with anti-F4/80-PE or FITC (Biolegend, BM8), anti-CD11b-APC or PE (eBioscience M1/70), anti-IL-1α-PE (eBioscience, ALF-161), anti-IL-1β-APC (eBioscience NJTEN3), anti-IL6 (eBioscience MP5-20F3), anti-TNF-α-PEcy5 (MP6-XT22 eBioscience), anti-IL-10-APC (eBioscience JESS-16E3), anti-Arg1-FITC (R&D Systems IC5868F) or isotype controls. All samples were run on a Guava easyCyte 8HT flow cytometer. Cells were gated on the forward and side scatter plot to remove debris, next on the $F4/80^+CD11b^+$ population and examined for cytokines. Macrophage numbers per colon were calculated by the percent of gated cells in relation to the overall number of cells per mouse colon.

Macrophage Culture:

Macrophages were extracted and cultured as previously described. (13) For macrophage-treated mice, $1\times10^6$ macrophages were injected IP on the first day of each DSS treatment (days 5, 26, 47) and on day 68.

Statistics:

Power analysis was performed to determine the sample size of the experimental and control groups to ensure that any effect, if one is in fact present, is statistically detectable. An alpha of 0.05 was used, and the minimum acceptable power was 0.80. A minimum of 5 animals per group (to allow for experimental error) at three independent experiments in vivo was used. Results were expressed as the mean±SE. Differences between means were evaluated by one-way ANOVA in GraphPad Prism 5. Values of $p<0.05$ were considered statistically significant.

Figure 1B:
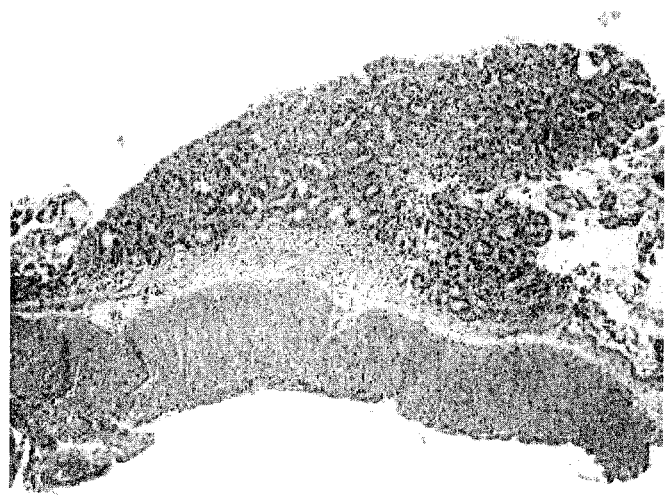
Figure 1C:
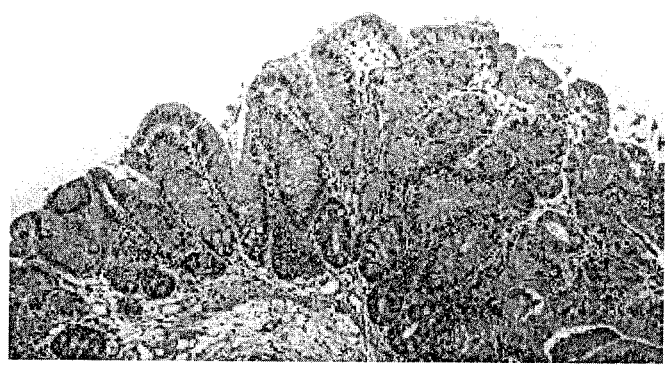
Figure 1D:
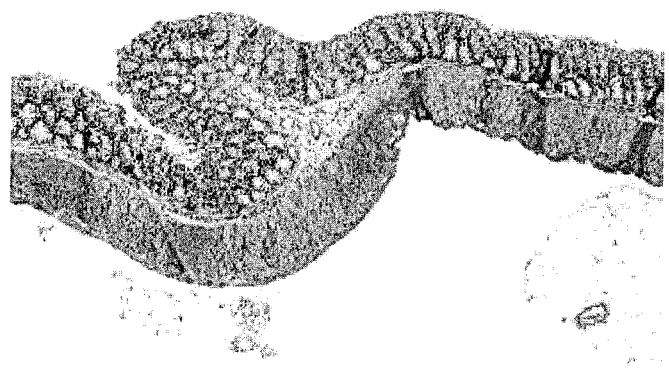
Figure 1E:
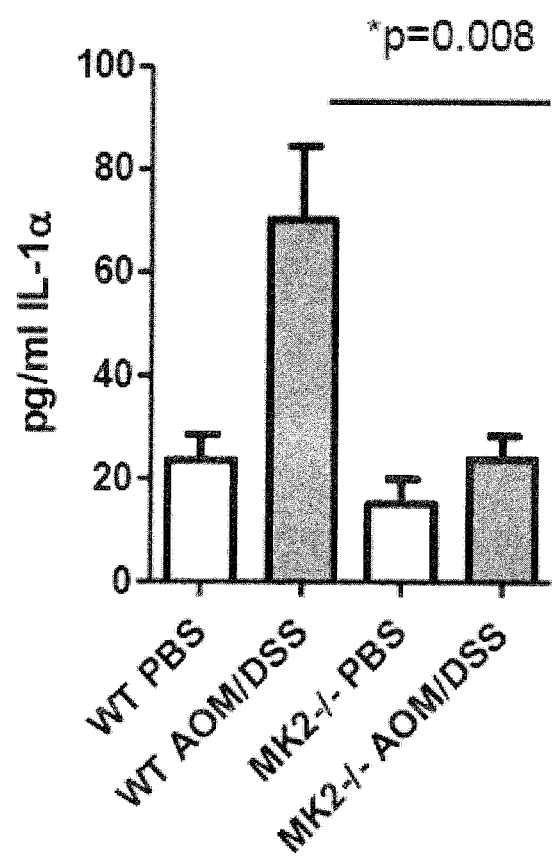
Figure 1F:
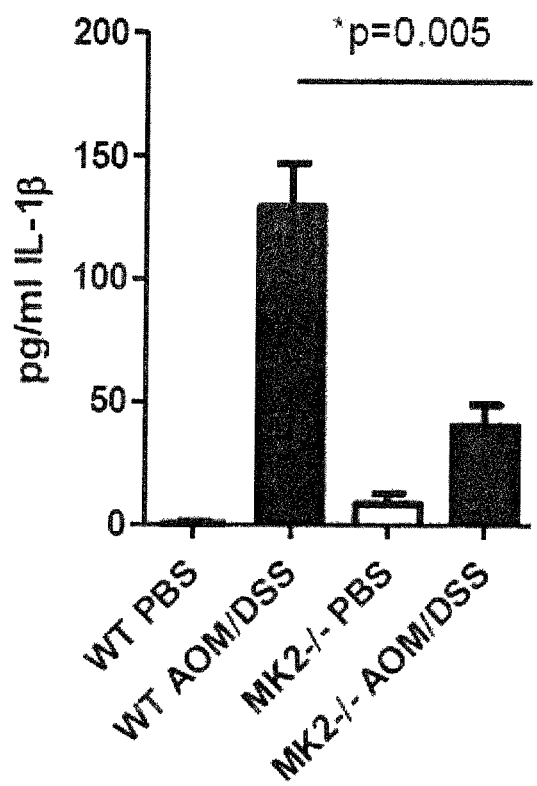
Figure 1G:
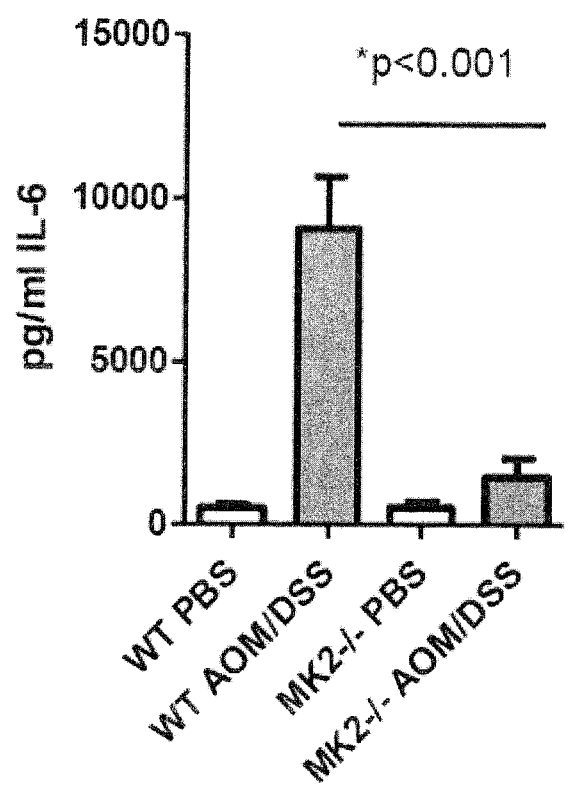
Figure 1H:
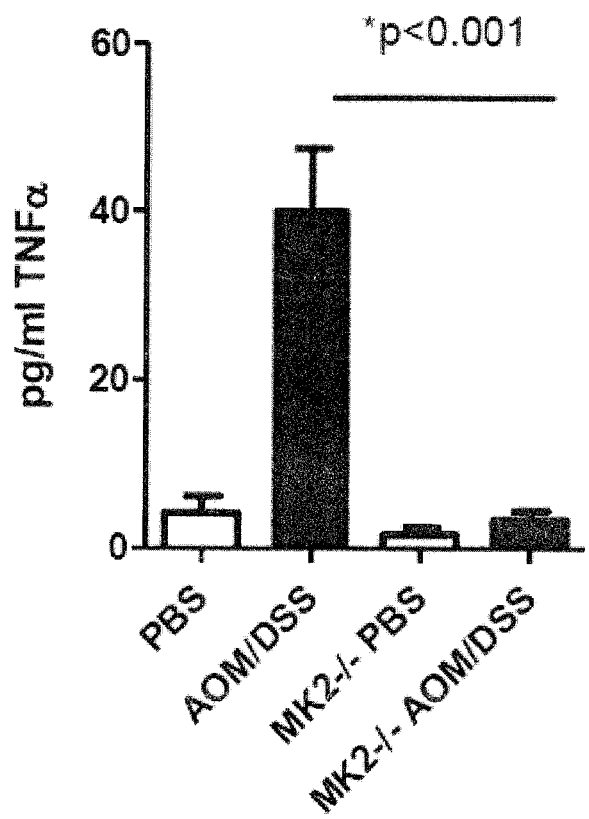

Results and Discussion:

MK2 is Essential for CAC Development:

Activation of MK2 leads to IL-1, IL-6, and TNF-α production. These cytokines are known to induce multiple cell survival and invasion pathways.(9-11) However, a specific role in cancer development has only been examined for MK2 in one study of skin cancer.(14) Thus, we set out to investigate pro-tumorigenic effects of MK2 in CAC. WT and $MK2^{-/-}$ mice were subjected to AOM and chronic treatments of DSS through three treatments and examined at day 80 as the commonly examined endpoint for this model. (15) Remarkably, $MK2^{-/-}$ mice did not develop neoplasms (FIG. 1A), while wild type mice had 100% incidence. Also, upon H&E staining, AOM/DSS treated WT mice developed well defined neoplasms with dysplastic proliferation of the colonic epithelium (FIG. 1B) and with DSS treatment had mild architectural disarray consistent with chronic injury (FIG. 1C). In contrast, $MK2^{-/-}$ mice treated with AOM/DSS displayed no signs of dysplasia (FIG. 1D). The complete absence of neoplasms in MK2-deficient mice after AOM and DSS-induced colitis indicate that MK2 is an important player in neoplasm development in CAC although the possibility exists that development could be delayed.

Cytokine Response is Substantially Reduced in $MK2^{-/-}$ Mice Exposed to AOM/DSS Compared to Wild Type Mice:

IL-1, IL-6 and TNF-α are major factors in the establishment of the IBD promoting chronic inflammation, and are also known as tumor promoting cytokines in CRC (16;17). Interestingly, $MK2^{-/-}$ mice display decreased IL-1, IL-6 and TNF-α production in multiple models.(18;19) Since these cytokines may be the major inflammatory mediators driving inflammation and neoplasm development, we hypothesized the lack of neoplasms in $MK2^{-/-}$ mice could be the result of a dampened inflammatory response. Conditioned media collected from AOM/DSS treated wild type mouse colon organ cultures in a previously described tissue explant approach used by multiple groups (20;21) displayed a marked increase in IL-1α, IL-1β, IL-6 and TNF-α compared to control mice receiving one PBS injection and regular water (FIGS. 1E-H). To further support the induction of MK2-downstream cytokines in mouse colons, we found a similar pattern of increase in IL-1α, IL-1β, IL-6 and TNF-α gene expression in WT AOM/DSS treated mice, but minimal induction in $MK2^{-/-}$ mice (Figure S1). These high levels (compared to PBS groups) of cytokines indicate a chronic inflammatory response in the colon due to multiple DSS treatments. Conversely, supernatant from colon tissues of $MK2^{-/-}$ mice treated with AOM/DSS displayed a significant reduction in these cytokines compared to WT AOM/DSS treated mice. These findings emphasize the importance of MK2 in regulating the production of inflammatory mediators that promote colon neoplasm development.

Figure 2A:
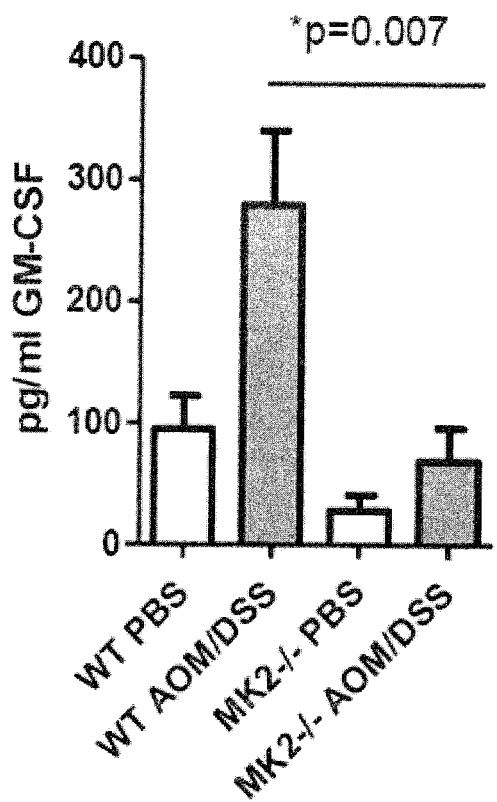
FIG. 2. Macrophages are a major source of MK2 downstream cytokines. Cytokines related to macrophage influx and function, A) GM-CSF and B) MCP-1 are substantially increased in AOM/DSS treated mice, but significantly decreased in MK2$^{-/-}$ mice. WT mice treated with AOM/DSS have increased C) F4/80$^+$CD11b$^+$ macrophage influx, which is substantially decreased in MK2$^{-/-}$ mice treated with AOM/DSS. F4/80$^+$CD11b$^+$ cells in MK2$^{-/-}$ mice also displayed significantly less intracellular staining of D) IL-1α, E) IL-1β, F) IL-6, G) TNF-α, H) IL-10, and I) ARG1 compared to WT mice. N=7 for WT mice and 8 for. MK2$^{-/-}$ mice in duplicate experiments.
Figure 2B:
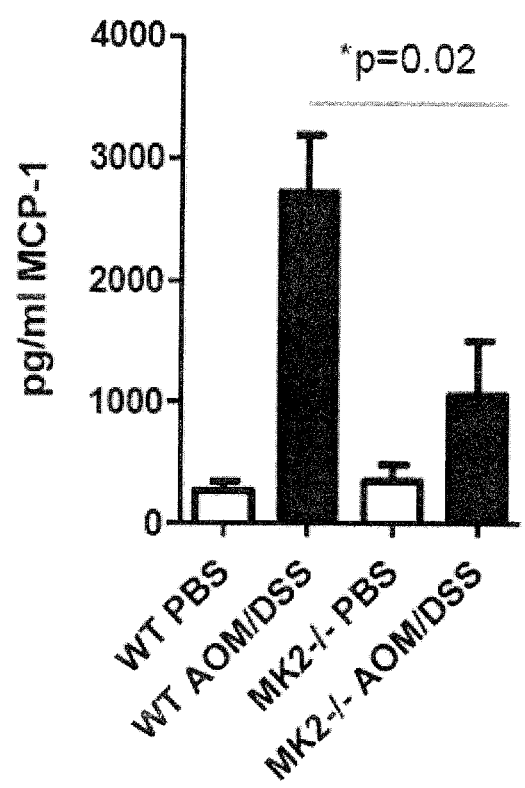
Figure 2D:
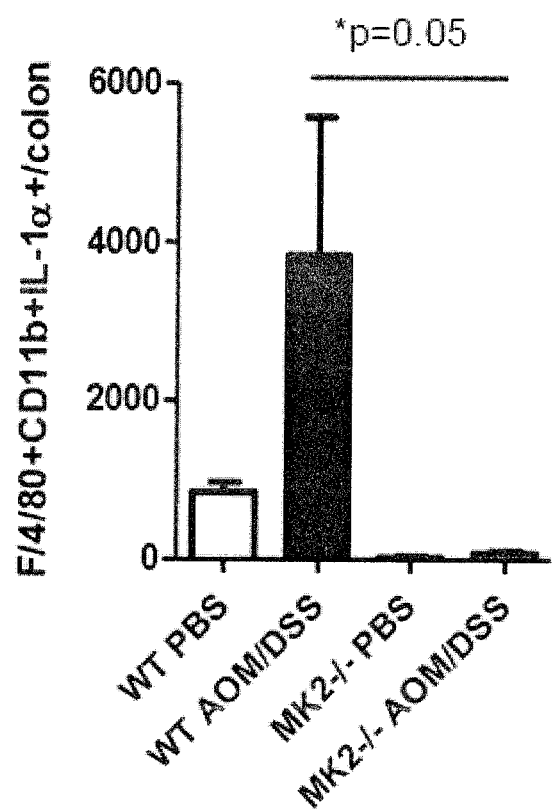
Figure 2E:
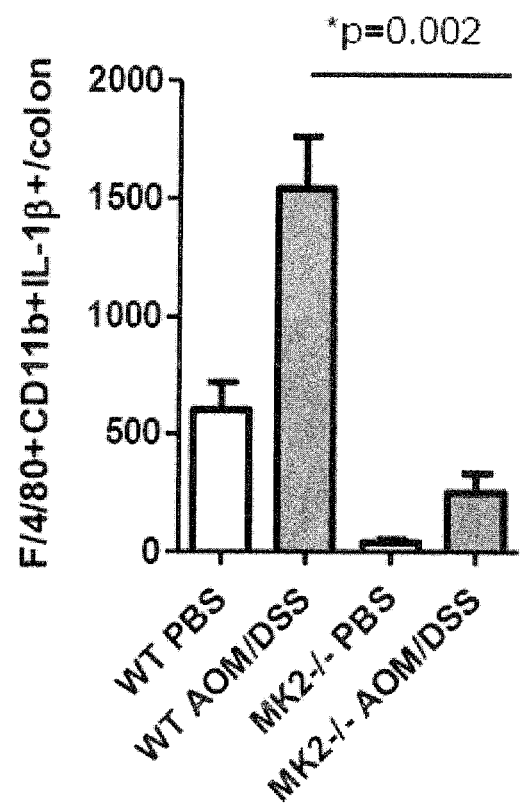
Figure 2F:
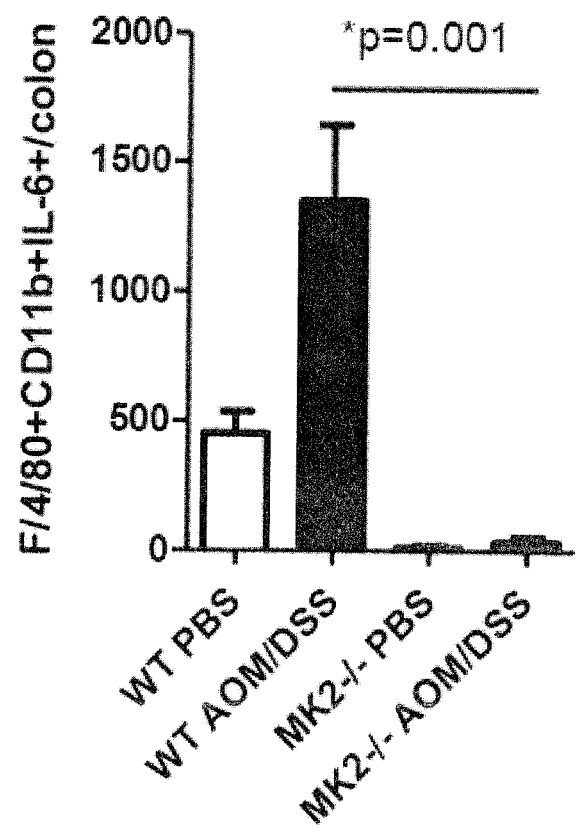
Figure 2G:
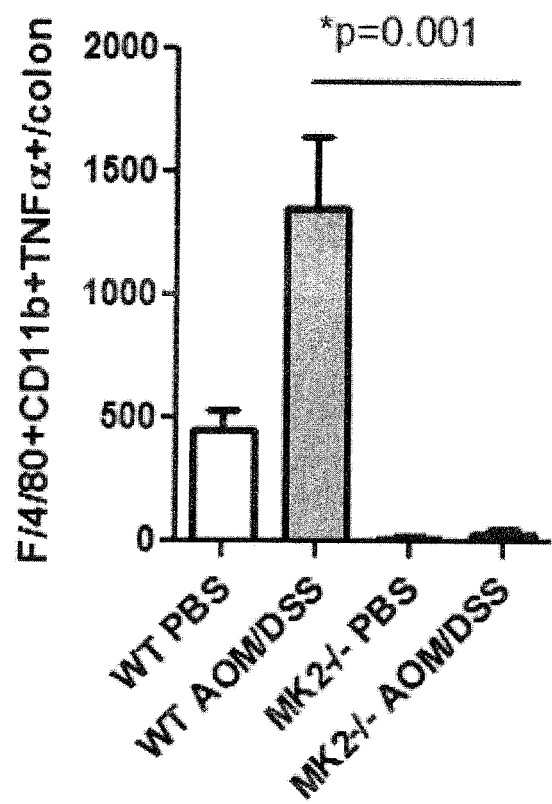
Figure 2H:
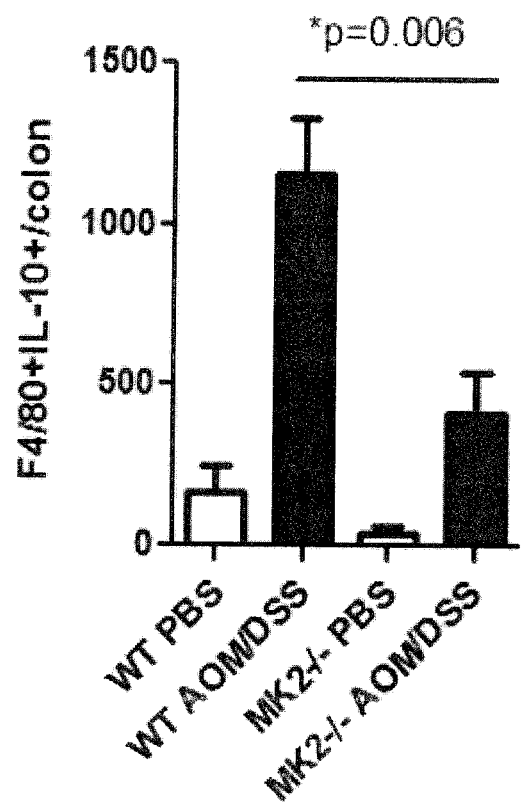
Figure 2I:
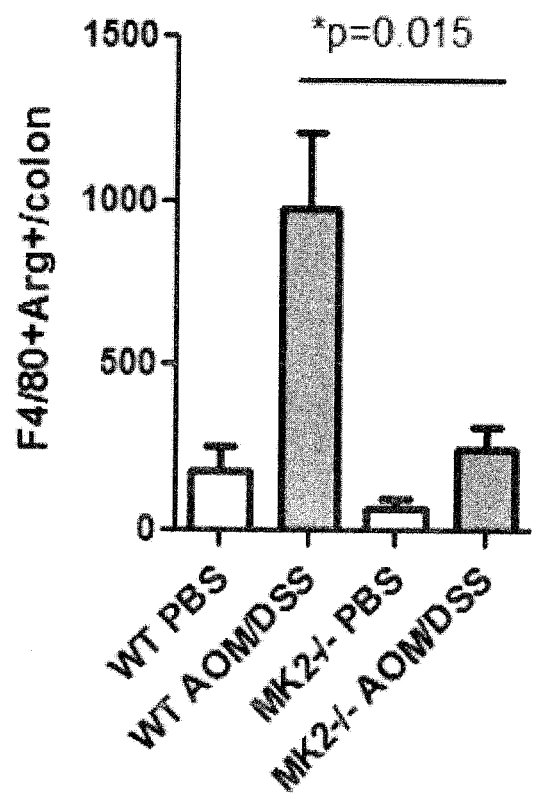

MK2 Deficiency Reduces Colonic Macrophage Accumulation and Cytokine Production in AOM/DSS Treated Mice:

The MK2 downstream cytokines IL-1, IL-6 and TNF-α are produced by multiple cell types, including macrophages, in the AOM/DSS model.(13) To examine the impact of macrophages in MK2-dependent inflammation and neoplasm development, we first examined factors related to macrophage accumulation and activation in mouse colon supernatants. GM-CSF and MCP-1 were substantially decreased in $MK2^{-/-}$ mice compared to WT mice administered AOM/DSS (FIGS. 2A and B). The expression of these factors is important for macrophage development and accumulation.(22;23) Due to the role of GM-CSF, MCP-1, IL-1, IL-6 and TNF-α in macrophage accumulation and activation, we assessed the number of colonic macrophages by staining single cell colon suspensions for F4/80 and CD11b. The amount of $F4/80^+CD11b^+$ cells found in the colon of AOM/DSS treated WT mice at day 80 was drastically increased in AOM/DSS treated WT mice compared to control groups, but markedly decreased in $MK2^{-/-}$ mice (FIG. 2C). To further understand the role of MK2 in macrophages localized in the colon of mice that have developed neoplasms, intracellular cytokines were examined after isolation and ex vivo stimulation. A substantial amount of macrophages isolated from colon preps of AOM/DSS treated WT mice expressed IL-1α, IL-1β, IL-6 and TNF-α compared to macrophages isolated from AOM/DSS treated $MK2^{-/-}$ mice (FIGS. 2D-G). The considerable decrease in colonic macrophages during CAC development in $MK2^{-/-}$ mice indicate the proper cells are not present in the colon to mount an inflammatory response to contribute to neoplasm development. We also found an increase in IL-10-expressing macrophages in WT AOM/DSS treated mice (FIG. 2H) and arginase-1 expressing macrophages (FIG. 2I), both of which were significantly decreased in $MK2^{-/-}$ mice. These data suggest that $MK2^{-/-}$ mice not only show a decrease in macrophages expressing MK2 downstream mediators, but are also decreased in macrophages producing M2-like pro-tumorigenic factors. In addition to macrophages, there are also other myeloid-derived cells that are attracted to the mouse colon during inflammation. Myeloid-derived suppressor cells (MDSC) have been found to contribute to colitis and colitis-associated tumor development and growth. Suppressing trafficking to the colon, or knocking out MDSC-associated activity reduces inflammation and tumor burden in the AOM/DSS model. (24;25) Thus, we also stained for MDSC (CD11b$^+$Gr1$^+$ cells). These cells were increased in WT mice treated with AOM/DSS compared to PBS and present at higher levels in WT than MK2$^{-/-}$ mice, but the difference did not achieve significance (Figure S2).

Figure 3A:
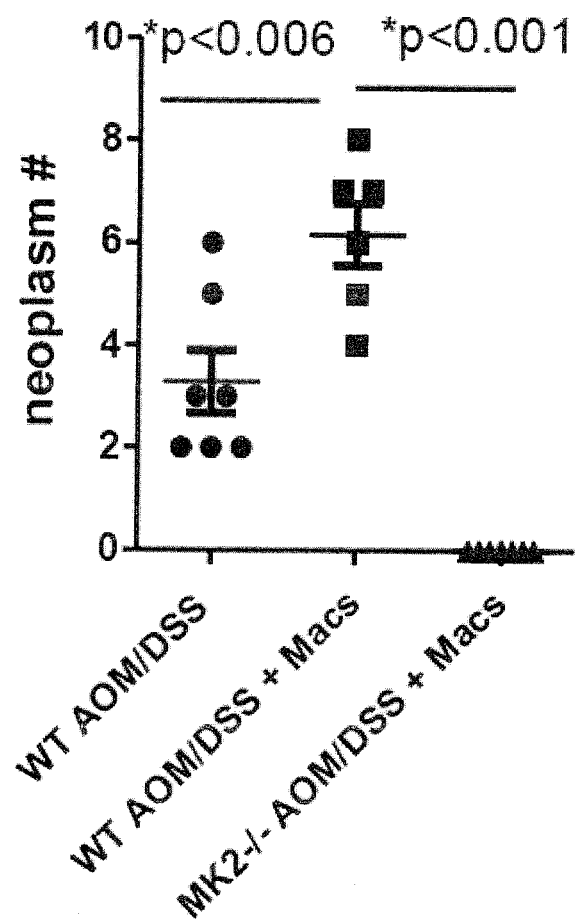
FIG. 3. WT BMM injection in MK2$^{-/-}$ mice restores some cytokine production, but not neoplasm development. BMM injections into WT and MK2$^{-/-}$ mice led to A) increased neoplasm development for WT mice, but not MK2$^{-/-}$ with AOM/DSS treatments. In organ culture, B) IL-1α, C) IL-1β, D) IL-6, E) TNF-α, F) GM-CSF, and G) MCP-1 production were found at higher levels in WT mice, but were also increased in MK2$^{-/-}$ mice supplemented with WT macrophages. N=6 for BMM supplementation experiments in duplicate experiments.
Figure 3B:
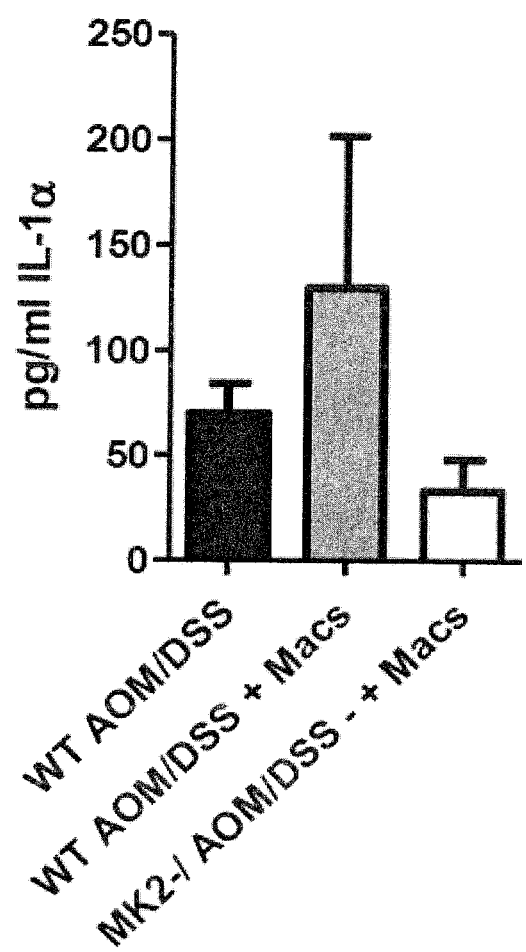
Figure 3C:
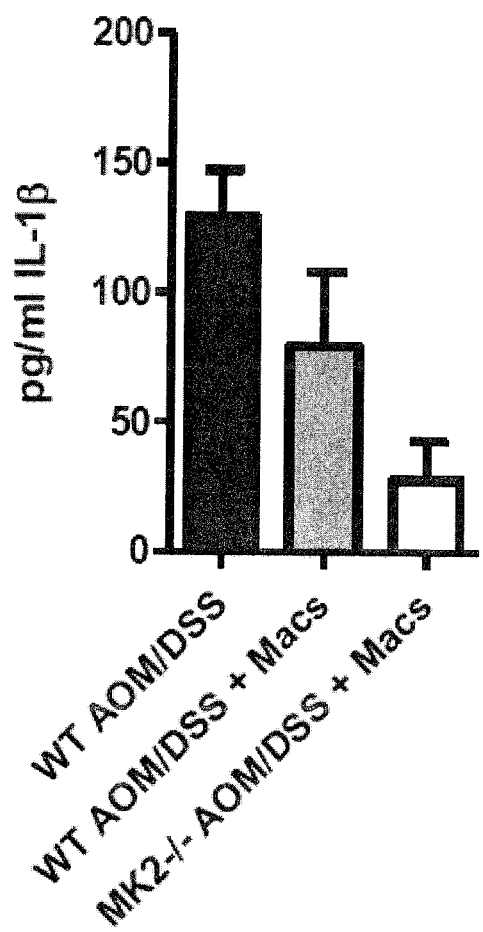
Figure 3E:
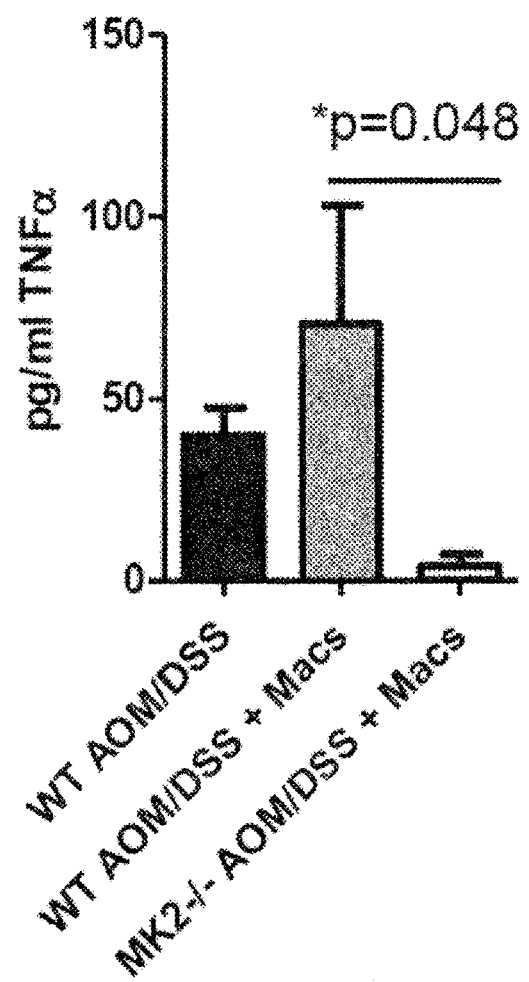
Figure 3F:
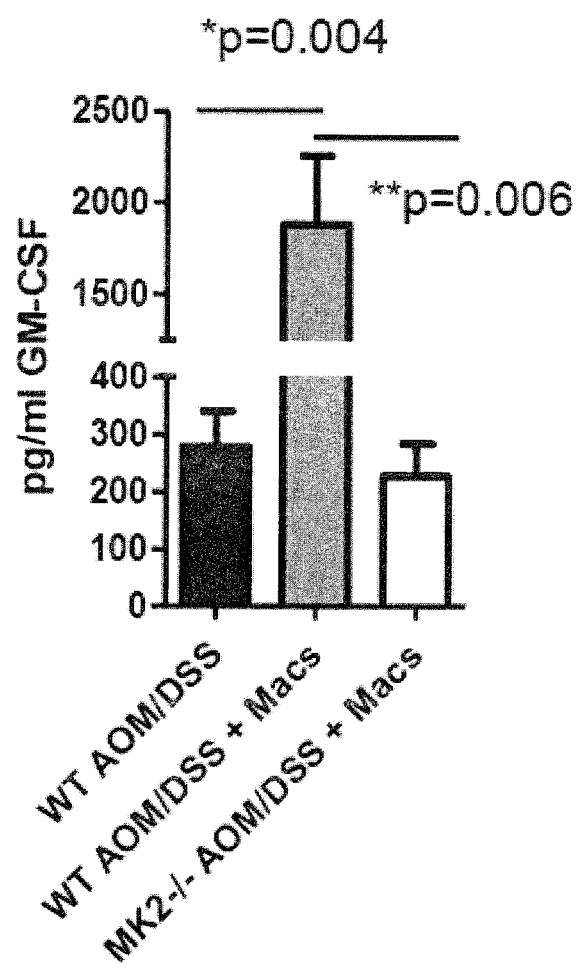
Figure 3G:
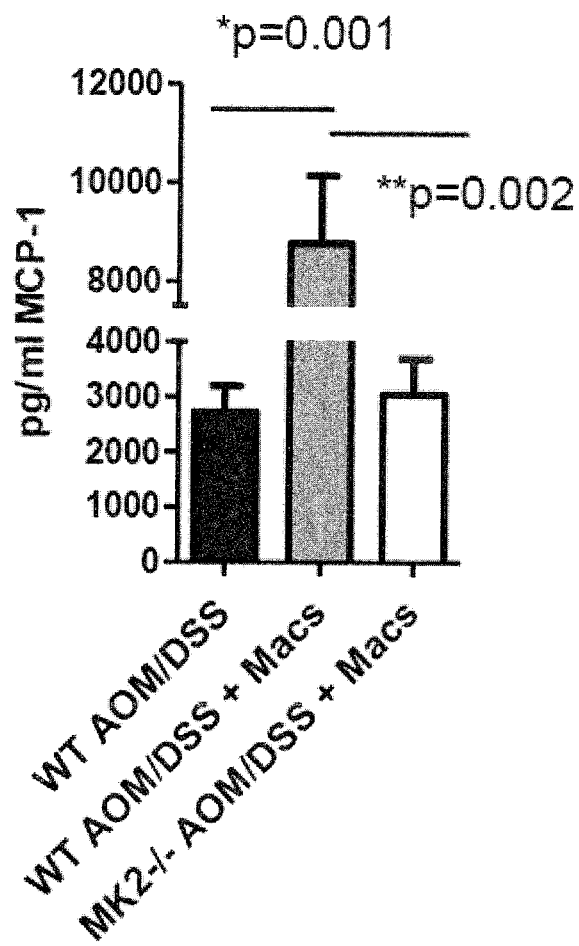
Figure 4:
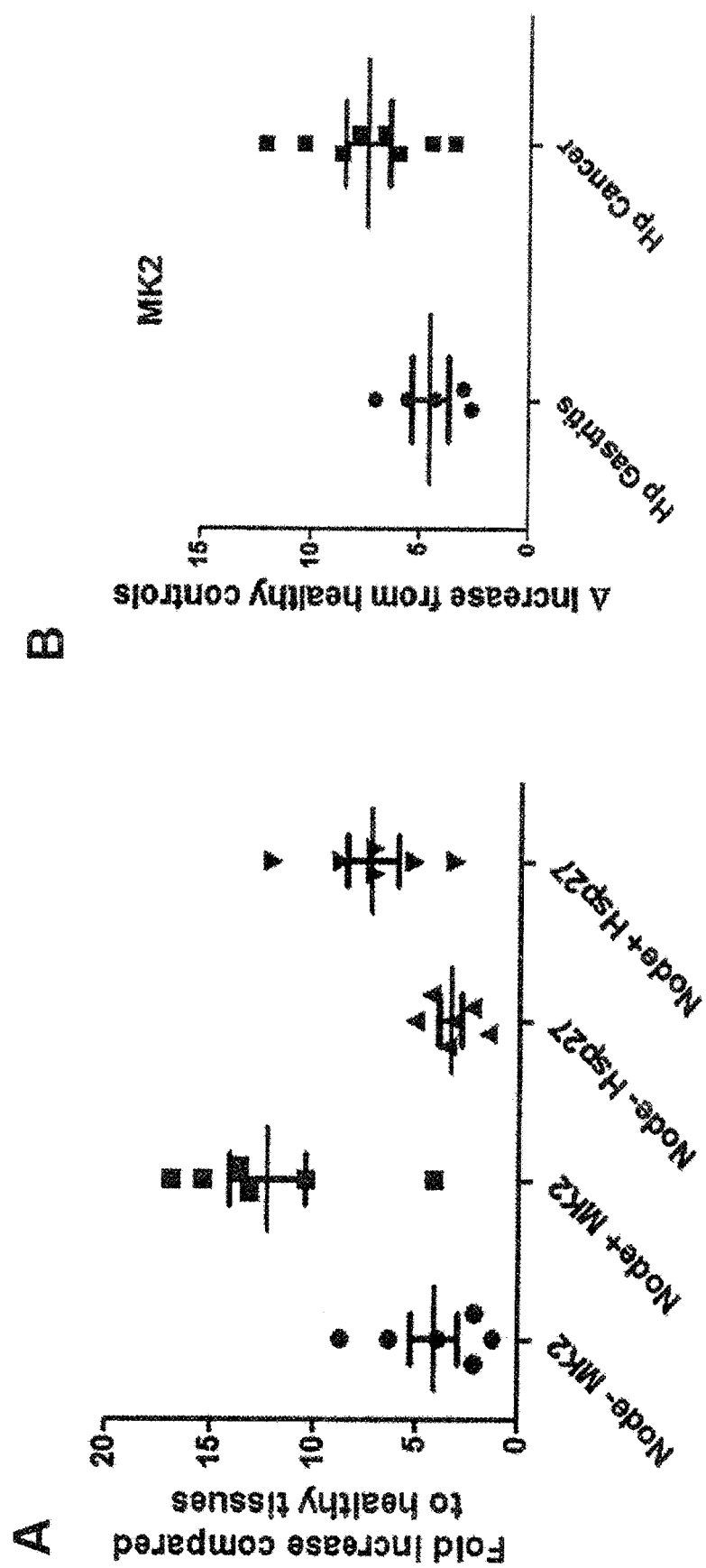
FIGS. 4A-B are graphs showing that human colon and gastric cancers have increased MK2 gene expression.
Figure 5A:
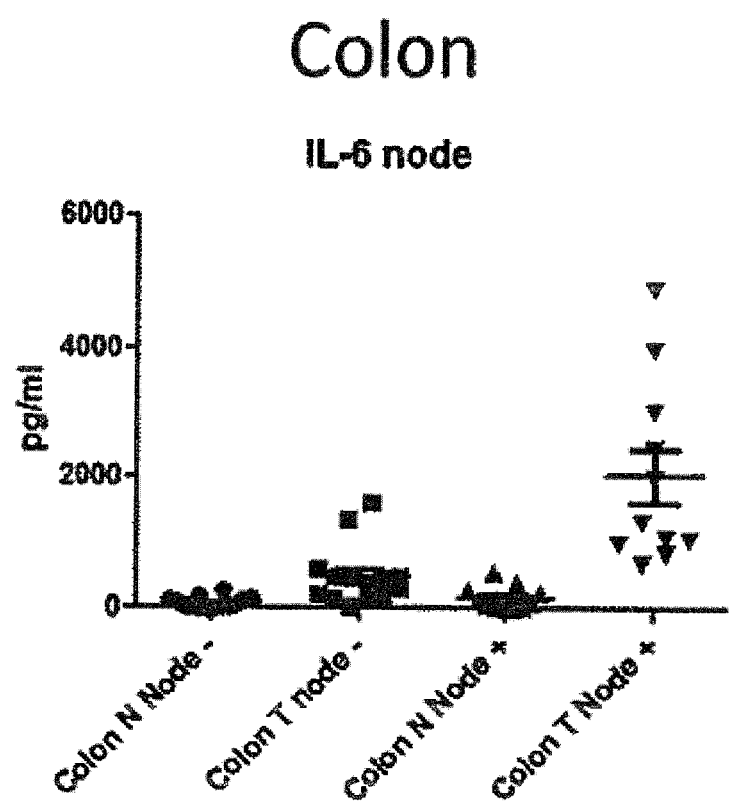
Figure 5B:
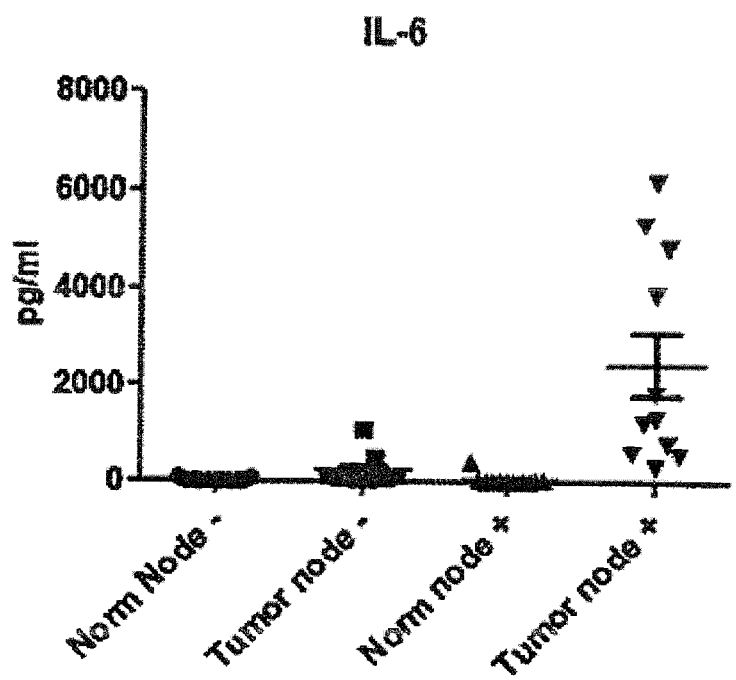
Figure 5D:
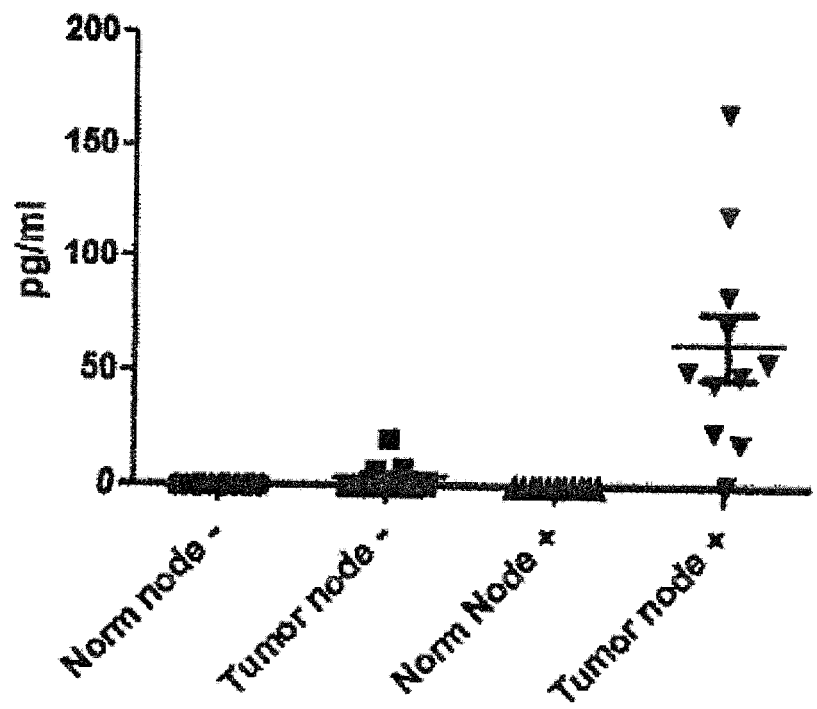
Figure 6:
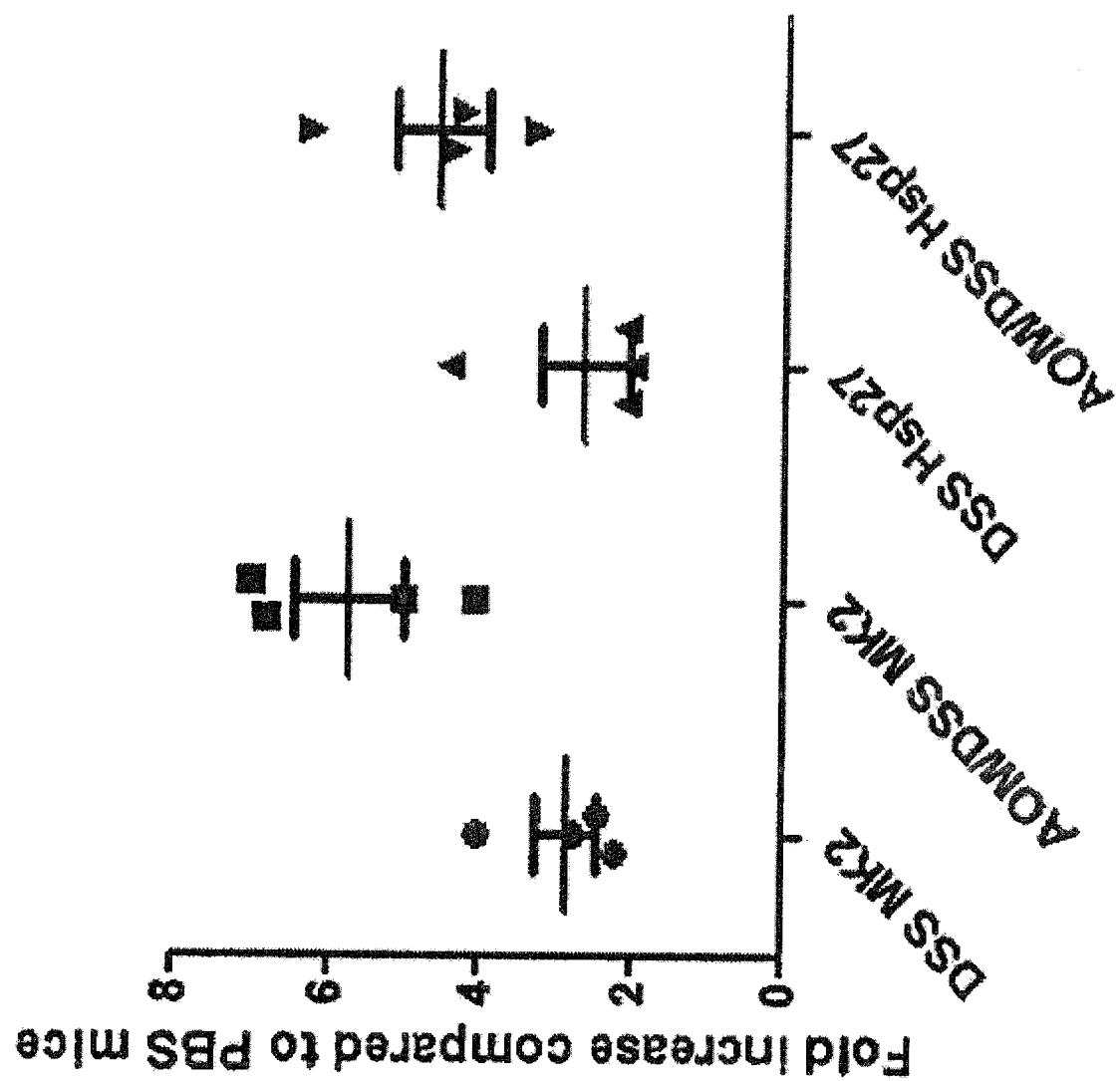
FIG. 6 is a graph showing that MK2 gene expression is increased in a mouse model of colorectal cancer. Mice treated with Azoxymethance (AOM)/Dextran sulfate sodium (DSS) for development of tumors have increased gene expression of MK2 and downstream Hsp27.
Figure 7:
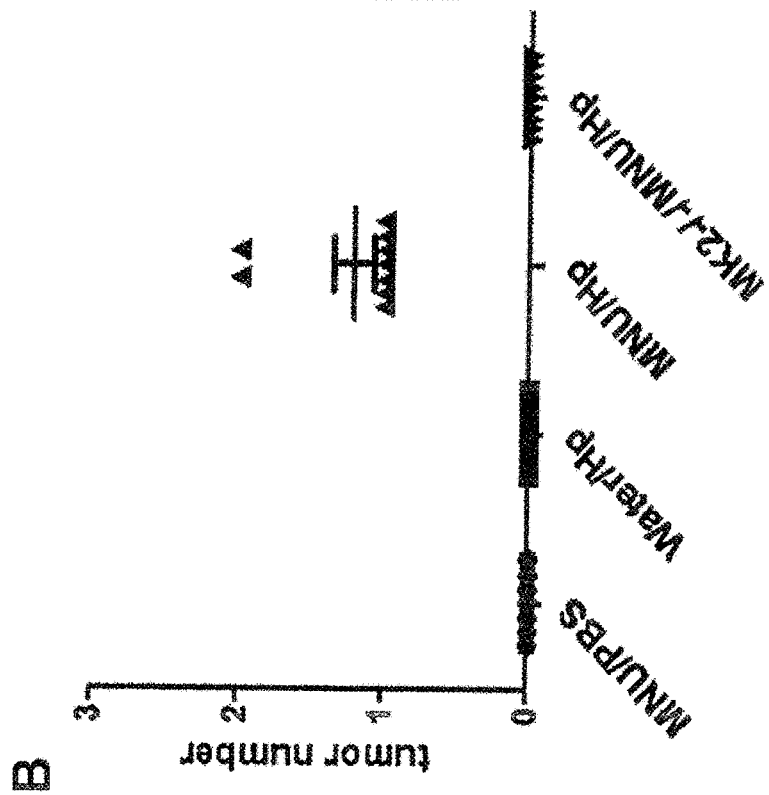
FIGS. 7A and 7B are graphs showing that MK2 knockout mice do not develop tumors in established models of gastric and colon cancer.
Figure 7:
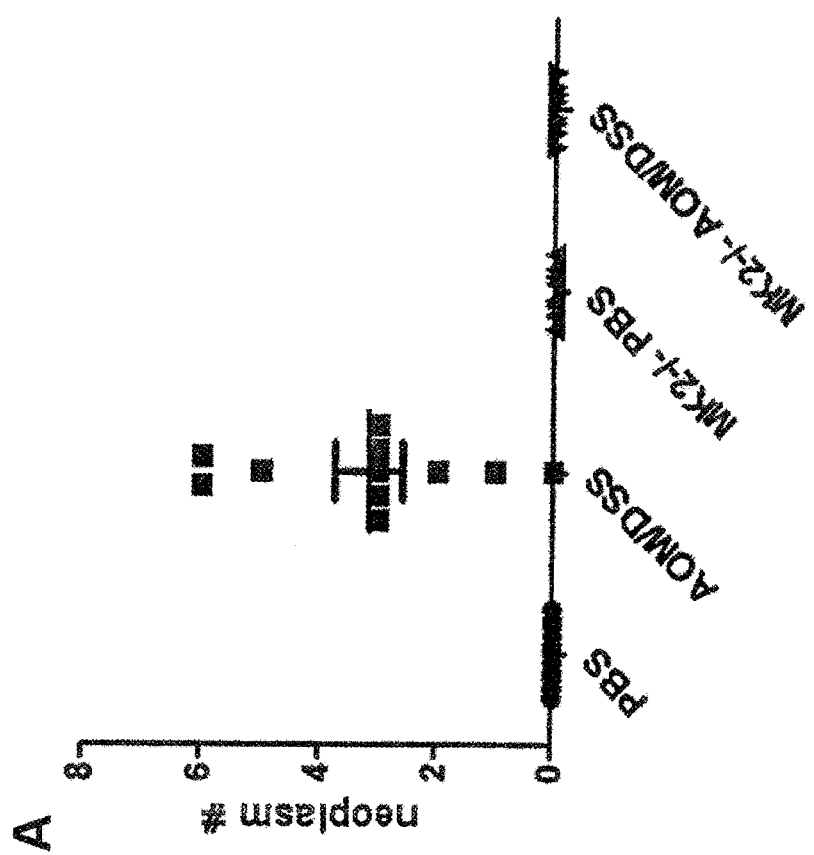
Figure 8:
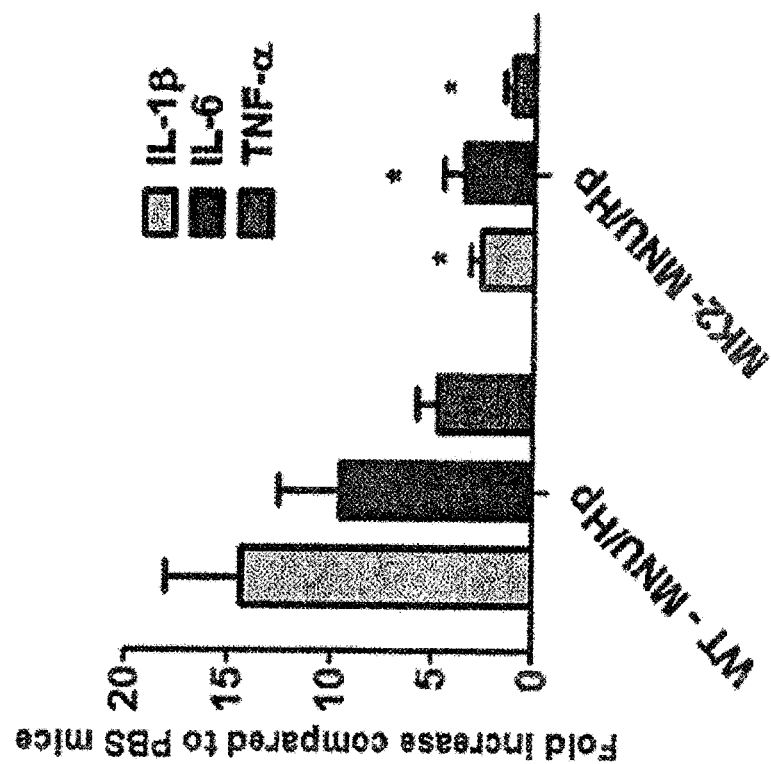
FIGS. 8A-C show that MK2 knockout mice have decreased production of MK2 downstream cytokines in established models of gastric and colon cancer.
Figure 8:
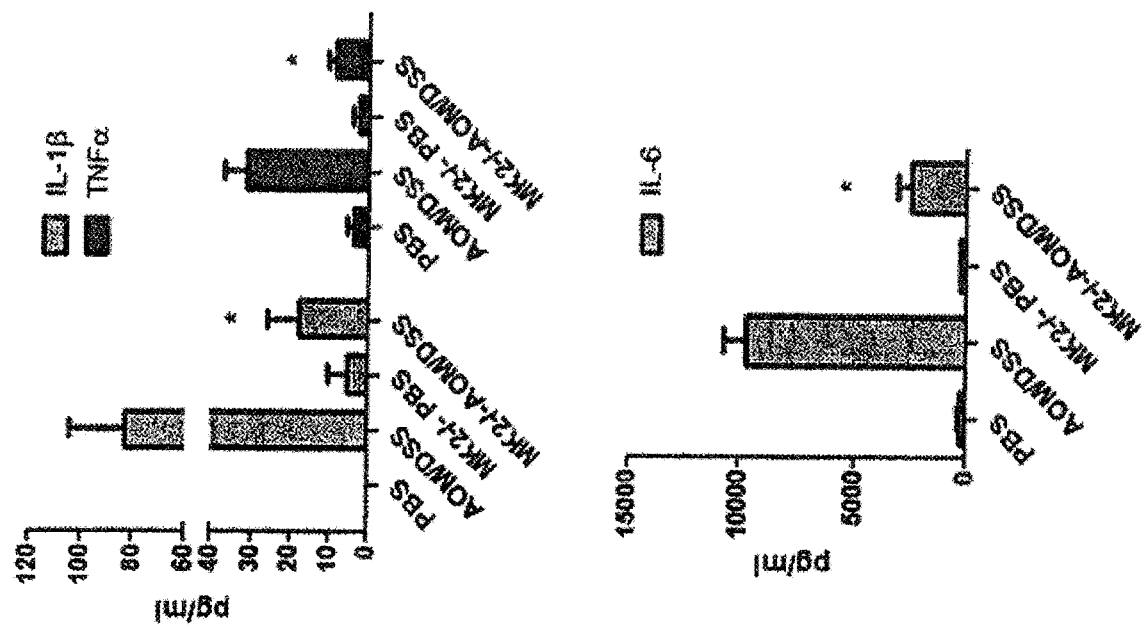
Figure 9:
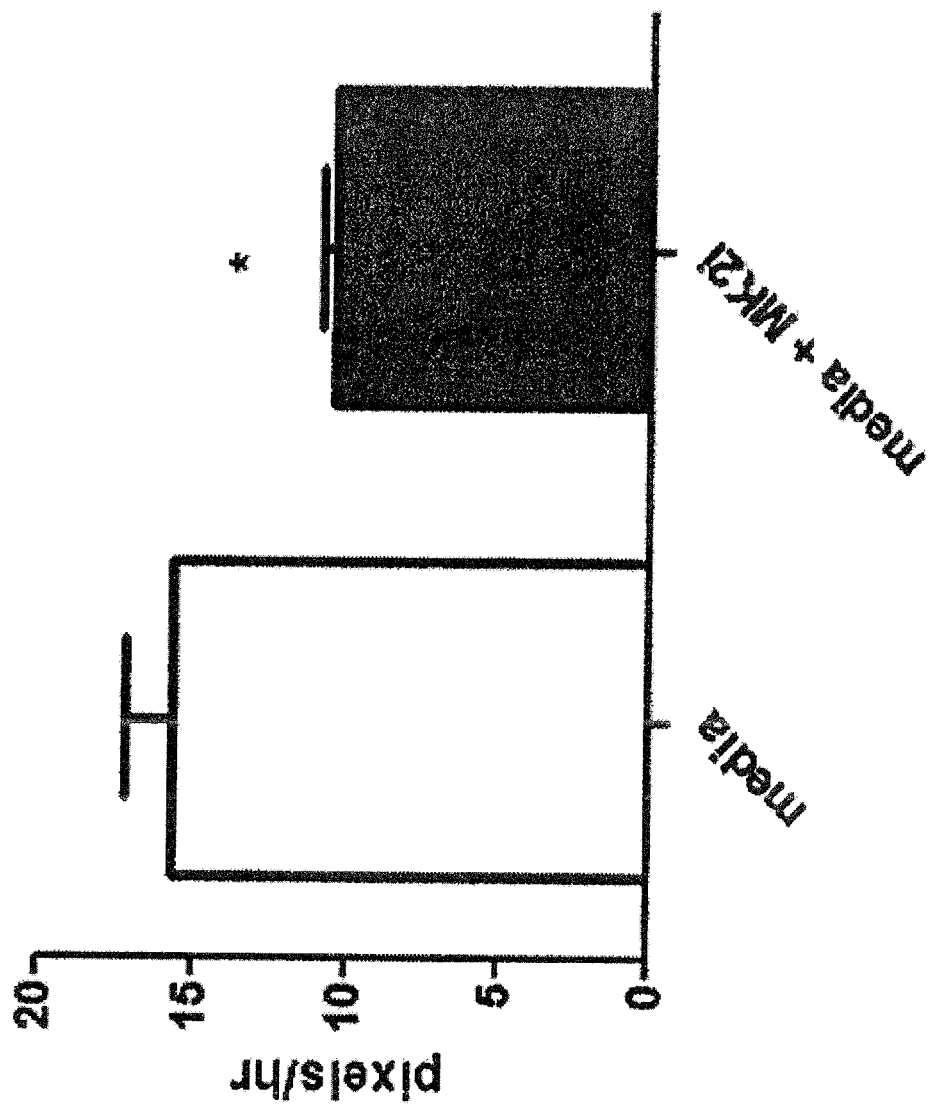
FIG. 9 is a graph showing that MK2 inhibition decreases colon cancer carcinoma cell proliferation. Incubating Caco-2 colon cancer cells with the MK2 inhibitor (MK2a) decreased proliferation and migration in a scratch wound assay.

Macrophages Enhance Pro-Inflammatory Cytokine Production, but not Neoplasm Development in AOM/DSS Treated Mice:

Macrophages harbor both anti- and pro-tumorigenic features that can hinder or enhance tumor formation. Our data above clearly indicate that macrophages accumulate and are producing MK2 downstream pro-inflammatory cytokines in tumor burden colons (FIG. 2). To assess the contribution of macrophage to CAC, bone marrow-derived macrophages (BMM) from WT mice were adoptively transferred into WT and MK2$^{-/-}$ AOM/DSS treated mice at days 5, 26, 47, and 68. Interestingly, AOM/DSS treated MK2$^{-/-}$ mice receiving WT BMM displayed no neoplasms, while an increased number of neoplasms were found in WT mice injected with WT BMM (FIG. 3A). WT mice receiving WT BMM had a mean of 6 neoplasms per mouse, while the WT mice had a mean of 3 neoplasms per mouse, which is a significant increase in number (p=0.006). These data indicate that macrophages promote neoplasm development in this system. Furthermore, addition of WT macrophages restored a proportion of the MK2 downstream cytokine production in MK2$^{-/-}$ mouse colons and also enhanced the amounts in WT mice receiving cells (FIGS. 3B-E). We further found an increase in the macrophage related cytokines GM-CSF and MCP-1 (FIGS. 3F and G). When comparing AOM/DSS treated MK2$^{-/-}$ mice supplemented with WT macrophages to AOM/DSS treated WT mice in FIGS. 1 and 2, IL-6, GM-CSF, and MCP-1 were drastically increased to similar levels, indicating the role of MK2 in promoting these responses. These data suggest that the number and frequency of BMM transfer into MK2$^{-/-}$ mice was adequate to mount a similar level of these cytokines as in wild type mice. IL-1α, IL-1β, and TNF-α were also increased upon WT BMM transfer into MK2$^{-/-}$ mice, but not to the same levels as WT mice suggesting that MK2 signaling in other cells may be responsible for production of these cytokines in WT mice. Introduction of WT macrophages into MK2$^{-/-}$ mice was not sufficient to restore neoplasm development indicating that MK2 is critical in other cells, perhaps epithelial cells, for neoplasm development. Furthermore, the significantly increased neoplasm development upon addition of extra macrophages into WT mice highlights the importance of MK2 signaling in macrophages in promoting tumor growth. Nevertheless, in our model, we have eliminated macrophages as being the primary determinant driving CAC development.

Our data highlight the importance of MK2 in CAC development and provide a target to hinder the inflammatory response. We demonstrate that restored MK2 signaling in a single cell type (macrophages) can restore the inflammatory response in MK2$^{-/-}$ mice and hence, this further substantiates the robustness of MK2 signaling pathway as a highly inflammatory event. Given the insurgence of reports demonstrating macrophages promote inflammation and cancer, we set out to the test hypothesis that MK2 in macrophages drives CAC development. The transfer of these cells was sufficient to restore the inflammatory response as determined by cytokine output (FIG. 3B-G). Nonetheless, restoration of MK2 in these cells (as well as the proinflammatory cytokines detected) was not sufficient to re-establish tumor development in MK2$^{-/-}$ mice. This suggests a more complex role for MK2 in CAC development where restoration of the inflammatory cytokines is only one part of the equation. Upon supplementation of macrophages to WT mice, neoplasm number was significantly increased (FIG. 3A). These data indicate that MK2-induced cytokines from macrophages promote increased tumor growth, but MK2 signaling is also needed in other cells, such as epithelial cells for tumor development. Thus, these studies raise the possibility that MK2 is a potential therapeutic target for patients with colitis or CAC that could prove beneficial.

REFERENCES

Siegel R, Naishadham D, Jemal A. Cancer statistics for Hispanics/Latinos, 2012. CA Cancer J Clin 2012; 62:283-98.

Dyson J K, Rutter M D. Colorectal cancer in inflammatory bowel disease: what is the real magnitude of the risk? World J Gastroenterol 2012; 18:3839-48.

Feng Y J, Li Y Y. The role of p38 mitogen-activated protein kinase in the pathogenesis of inflammatory bowel disease. J Dig Dis 2011; 12:327-32.

Genovese M C. Inhibition of p38: has the fat lady sung? Arthritis Rheum 2009; 60:317-20.

Xu J J, Hendriks B S, Zhao J, de G D. Multiple effects of acetaminophen and p38 inhibitors: towards pathway toxicology. FEBS Lett 2008; 582:1276-82.

Morris D L, O'Neil S P, Devraj R V, Portanova J P, Gilles R W, Gross C J, Curtiss S W, Komocsar W J, Garner D S, Happa F A, Kraus L J, Nikula K J, et al. Acute lymphoid and gastrointestinal toxicity induced by selective p38alpha map kinase and map kinase-activated protein kinase-2 (MK2) inhibitors in the dog. Toxicol Pathol 2010; 38:606-18.

Seimon T A, Wang Y, Han S, Senokuchi T, Schrijvers D M, Kuriakose G, Tall A R, Tabas I A. Macrophage deficiency of p38alpha MAPK promotes apoptosis and plaque necrosis in advanced atherosclerotic lesions in mice. J Clin Invest 2009; 119:886-98.

Kotlyarov A, Yannoni Y, Fritz S, Laass K, Telliez J B, Pitman D, Lin L L, Gaestel M. Distinct cellular functions of MK2. Mol Cell Biol 2002; 22:4827-35.

Garlanda C, Riva F, Veliz T, Polentarutti N, Pasqualini F, Radaelli E, Sironi M, Nebuloni M, Zorini E O, Scanziani E, Mantovani A. Increased susceptibility to colitis-associated cancer of mice lacking TIR8, an inhibitory member of the interleukin-1 receptor family. Cancer Res 2007; 67:6017-21.

Grivennikov S, Karin E, Terzic J, Mucida D, Yu G Y, Vallabhapurapu S, Scheller J, Rose-John S, Cheroutre H, Eckmann L, Karin M. IL-6 and Stat3 are required for survival of intestinal epithelial cells and development of colitis-associated cancer. Cancer Cell 2009; 15:103-13.

Mantovani A. Molecular pathways linking inflammation and cancer. Curr Mol Med 2010; 10:369-73.

Steinbach E C, Plevy S E. The role of macrophages and dendritic cells in the initiation of inflammation in IBD. Inflamm Bowel Dis 2014; 20:166-75.

Zhang X, Goncalves R, Mosser D M. The isolation and characterization of murine macrophages. Curr Protoc Immunol 2008; Chapter 14.

Johansen C, Vestergaard C, Kragballe K, Kollias G, Gaestel M, Iversen L. MK2 regulates the early stages of skin tumor promotion. Carcinogenesis 2009; 30:2100-8.

Neufert C, Becker C, Neurath M F. An inducible mouse model of colon carcinogenesis for the analysis of sporadic and inflammation-driven tumor progression. Nat Protoc 2007; 2:1998-2004.

Guven M E, Keskin O, Gursoy A, Nussinov R. The structural network of inflammation and cancer: merits and challenges. Semin Cancer Biol 2013; 23:243-51.

Strober W, Fuss I J. Proinflammatory cytokines in the pathogenesis of inflammatory bowel diseases. Gastroenterology 2011; 140:1756-67.

Ronkina N, Kotlyarov A, Dittrich-Breiholz O, Kracht M, Hitti E, Milarski K, Askew R, Marusic S, Lin L L, Gaestel M, Telliez J B. The mitogen-activated protein kinase (MAPK)-activated protein kinases MK2 and MK3 cooperate in stimulation of tumor necrosis factor biosynthesis and stabilization of p38 MAPK. Mol Cell Biol 2007; 27:170-81.

Tietz A B, Malo A, Diebold J, Kotlyarov A, Herbst A, Kolligs F T, Brandt-Nedelev B, Halangk W, Gaestel M, Goke B, Schafer C. Gene deletion of MK2 inhibits TNF-alpha and IL-6 and protects against cerulein-induced pancreatitis. Am J Physiol Gastrointest Liver Physiol 2006; 290:G1298-G1306.

Randall K J, Turton J, Foster J R. Explant culture of gastrointestinal tissue: a review of methods and applications. Cell Biol Toxicol 2011; 27:267-84.

Sheikh S Z, Matsuoka K, Kobayashi T, Li F, Rubinas T, Plevy S E. Cutting edge: IFN-gamma is a negative regulator of IL-23 in murine macrophages and experimental colitis. J Immunol 2010; 184:4069-73.

Francisco-Cruz A, Aguilar-Santelises M, Ramos-Espinosa O, Mata-Espinosa D, Marquina-Castillo B, Barrios-Payan J, Hernandez-Pando R. Granulocyte-macrophage colony-stimulating factor: not just another haematopoietic growth factor. Med Oncol 2014; 31:774.

Zhang J, Patel L, Pienta K J. CC chemokine ligand 2 (CCL2) promotes prostate cancer tumorigenesis and metastasis. Cytokine Growth Factor Rev 2010; 21:41-8.

Katoh H, Wang D, Daikoku T, Sun H, Dey S K, Dubois R N. CXCR2-expressing myeloid-derived suppressor cells are essential to promote colitis-associated tumorigenesis. Cancer Cell 2013; 24:631-44.

Ichikawa M, Williams R, Wang L, Vogl T, Srikrishna G. S100A8/A9 activate key genes and pathways in colon tumor progression. Mol Cancer Res 2011; 9:133-48.

The invention claimed is:

1. A method of treating cancer in a patient in need comprising administering to said patient an effective amount of a pharmaceutical composition comprising an effective amount of MK2 inhibitor BIO-475863 (CAS-41179-33-3) or PF-3644022 according to the chemical structure:

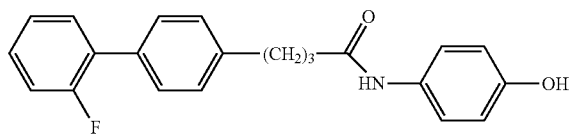

BIO-475863 or

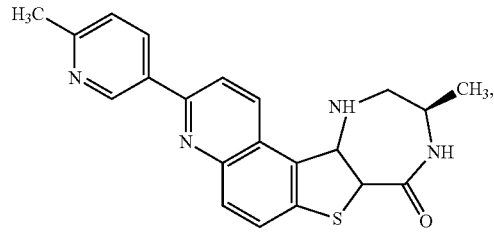

PF-3644022 or a pharmaceutically acceptable salt or hydrate thereof; wherein said cancer is colorectal cancer, gastric cancer, head and neck cancer or lung cancer which overexpresses MK2 compared to normal tissue.

2. The method according to claim 1 wherein said cancer is metastatic cancer.

3. The method according to claim 1 wherein said cancer is recurrent cancer.

4. The method according to claim 1 wherein said cancer is colorectal cancer or head and neck cancer.

5. The method according to claim 1 wherein said cancer is colorectal cancer or gastric cancer.

6. The method according to claim 1 wherein said cancer is colorectal cancer or lung cancer.

7. The method according to claim 2 wherein said cancer is colorectal cancer or head and neck cancer.

8. The method according to claim 2 wherein said cancer is colorectal cancer or gastric cancer.

9. The method according to claim 2 wherein said cancer is colorectal cancer or lung cancer.

10. The method according to claim 3 wherein said cancer is colorectal cancer or head and neck cancer.

11. The method according to claim 3 wherein said cancer is colorectal cancer or gastric cancer.

12. The method according to claim 3 wherein said cancer is colorectal cancer or lung cancer.

13. The method according to claim 1 wherein said inhibitor is administered in combination with an additional anticancer agent wherein said additional anticancer agent is 5-fluorouracil (5-FU).

14. The method according to claim 1 which is combined with radiation therapy.

15. The method according to claim 2 which is combined with radiation therapy.

16. The method according to claim 3 which is combined with radiation therapy.

17. The method according to claim 4 which is combined with radiation therapy.

18. The method according to claim 7 which is combined with radiation therapy.

19. The method according to claim 10 which is combined with radiation therapy.

20. The method according to claim 1 wherein said compound is PF-3644022 or a pharmaceutically acceptable salt or hydrate thereof.

* * * * *

SEQUENCE LISTING

```
<160> NUMBER OF SEQ ID NOS: 1

<210> SEQ ID NO 1
<211> LENGTH: 23
<212> TYPE: PRT
<213> ORGANISM: Homo sapiens

<400> SEQUENCE: 1

Trp Leu Arg Arg Ile Lys Ala Trp Leu Arg Arg Ile Lys Ala Leu Asn
1               5                   10                  15

Arg Gln Leu Gly Val Ala Ala
            20
```